US009469836B2

(12) United States Patent
Miller et al.

(10) Patent No.: US 9,469,836 B2
(45) Date of Patent: Oct. 18, 2016

(54) **ANTIFUNGAL METABOLITES FROM FUNGAL ENDOPHYTES OF *PINUS STROBUS***

(75) Inventors: John David Miller, Ottawa (CA); Greg William Adams, Sussex Corner (CA); Mark Sumarah, Ottawa (CA)

(73) Assignee: J.D. IRVING, LIMITED, St. John (CA)

( * ) Notice: Subject to any disclaimer, the term of this patent is extended or adjusted under 35 U.S.C. 154(b) by 790 days.

(21) Appl. No.: 13/360,240

(22) Filed: Jan. 27, 2012

(65) Prior Publication Data

US 2012/0198590 A1    Aug. 2, 2012

Related U.S. Application Data

(60) Provisional application No. 61/437,468, filed on Jan. 28, 2011.

(51) Int. Cl.

| | | |
|---|---|---|
| *A01N 49/00* | (2006.01) | |
| *C12N 1/14* | (2006.01) | |
| *C07D 309/06* | (2006.01) | |
| *C07D 321/00* | (2006.01) | |
| *C12P 7/22* | (2006.01) | |
| *C12P 7/40* | (2006.01) | |
| *C12P 17/08* | (2006.01) | |
| *C12R 1/645* | (2006.01) | |
| *C07C 39/19* | (2006.01) | |
| *A01N 43/16* | (2006.01) | |
| *A01N 37/42* | (2006.01) | |
| *A01N 43/24* | (2006.01) | |

(52) U.S. Cl.
CPC ............... *C12N 1/14* (2013.01); *A01N 37/42* (2013.01); *A01N 43/16* (2013.01); *A01N 43/24* (2013.01); *A01N 49/00* (2013.01); *C07C 39/19* (2013.01); *C07D 309/06* (2013.01); *C07D 321/00* (2013.01); *C12P 7/22* (2013.01); *C12P 7/40* (2013.01); *C12P 17/08* (2013.01); *C12R 1/645* (2013.01)

(58) Field of Classification Search
None
See application file for complete search history.

(56) References Cited

U.S. PATENT DOCUMENTS

| | | | |
|---|---|---|---|
| 4,940,834 A | 7/1990 | Hurley et al. | |
| 5,723,720 A | 3/1998 | Brede et al. | |
| 5,880,343 A | 3/1999 | Hiruma et al. | |
| 6,180,855 B1 | 1/2001 | Hiruma et al. | |
| 6,911,338 B2 | 6/2005 | Strobel et al. | |
| 7,037,879 B2 | 5/2006 | Imada et al. | |
| 7,070,985 B2 | 7/2006 | Strobel et al. | |
| 7,084,331 B2 | 8/2006 | Isawa et al. | |
| 7,192,939 B2 | 3/2007 | Strobel et al. | |
| 7,214,509 B2 | 5/2007 | Schnoor et al. | |
| 2003/0186425 A1 | 10/2003 | Strobel et al. | |
| 2004/0018168 A1 | 1/2004 | Strobel et al. | |
| 2004/0141955 A1 | 7/2004 | Strobel et al. | |
| 2004/0185031 A1 | 9/2004 | Strobel et al. | |
| 2004/0206697 A1 | 10/2004 | Strobel et al. | |
| 2005/0150024 A1 | 7/2005 | West et al. | |
| 2005/0220769 A1 | 10/2005 | Strobel et al. | |
| 2006/0019295 A1 | 1/2006 | Presting | |
| 2006/0121593 A1 | 6/2006 | Christensen et al. | |
| 2006/0127346 A1 | 6/2006 | Strobel et al. | |
| 2006/0127347 A1 | 6/2006 | Strobel et al. | |
| 2006/0134762 A1 | 6/2006 | Puri et al. | |
| 2007/0006341 A1 | 1/2007 | Wagner et al. | |
| 2007/0010461 A1 | 1/2007 | Chibber | |
| 2007/0118927 A1 | 5/2007 | Bryan et al. | |
| 2007/0142226 A1 | 6/2007 | Franco | |

FOREIGN PATENT DOCUMENTS

| | | |
|---|---|---|
| WO | 90/13224 A1 | 11/1990 |
| WO | 20051009360 | 2/2005 |

OTHER PUBLICATIONS

Bucheli et al 2000, J. Evol. Biol. 13: 188-198.*
Ganley et al 2006, Micological Research 110: 318-327.*
Miller et al 2009, Fungal Ecology 2:98-101.*
Sumarah et al 2008, Mycological Research 112:731-736.*
Ganley et al 2008, Forest Ecology and Management 255:2751-2760.*
Serra Stefano, Bisabolane Sesquiterpenes: Synthesis of (R)-(+)-Sydowic Acid and (R)-(+)-Curcumene Ether. Synlett 2000, No. 6, 890-892.
Miller, J.D., et al. "Needles of white spruce inoculated with rugulosin-producing endophytes contain rugulosin reducing spruce budworm growth rate". Myocol. Res. Apr. 2002. vol. 106, No. 4, pp. 471-479, ISSN: 0953-7565.
Sumarah M.W. et al. "Measurement of a rugulosin-producing endophyte in white spruce seedlings". Mycolgia. 2005. vol. 97, No. 4, pp. 770-776, ISSN:1557-2536.
Stefani, F.O.P., and Berube J.A. Genbank Acc. No. AY561216. May 26, 2004.
Watanabe, K. et al. Genbank Acc. No. AB179774. Nov. 17, 2004.
Sokolski, S. et al. Genbank Acc. No. AY971727. Apr. 18, 2005.
Lim, Y.W. et al. Genbank Acc. No. AY761179. Sep. 30, 2005.
Sokolski, S. et al. Genbank Acc. No. AY971709. Apr. 18, 2005.

(Continued)

*Primary Examiner* — David H Kruse

(74) *Attorney, Agent, or Firm* — Bereskin & Parr LLP; Carmela De Luca

(57) ABSTRACT

The disclosure pertains to isolated white pine toxigenic endophytes and the compounds produced by the fungal endophytes as well as methods and uses of the white pine endophytes. The isolated white pine toxigenic endophytes are useful for preparing white pine seedlings and plants that have increased tolerance to a pest and are prepared by inoculating a white pine seedling during the susceptible time window.

24 Claims, 6 Drawing Sheets

(56) References Cited

OTHER PUBLICATIONS

Sokolski, S. et al. "A fungal endophyte of black spruce (*Picea mariana*) needles is also an aquatic hyphomycete". Mol. Ecol. Jun. 2006, vol. 15, No. 7, pp. 1955-1962, ISSN:1471-8278 (Genbank Acc. Nos. AY746345, AY746350, and AY746341).
Lygis, V. et al. "Silvicultural and pathological evaluation of Scots pine afforestations mixed with deciduous trees to reduce the infections by *Heterobasidion annosum* s.s", For. Ecol. Manage. 2004. vol. 201, Nos. 2-3, pp. 275-185, ISSN:0378-1127 (Genbank Acc. No. AY590791).
Sokolski, S. et al. Genbank Acc. No. AY971690, Apr. 18, 2005.
Sanchez Marquez, S. et al. Genbank Acc. No. AM262390, May 12, 2006.
Ganley, R.J. and Newcombe, G. "Fungal endophytes in seeds and needles of *Pinus monticola*". Mycol. Res. Mar. 2006. vol. 100 (part 3), pp. 318-327, ISSN:0953-7562 (Genbank Acc. No. AY465453).
Hoffman, M.T. and Arnold, A.E., Genbank Acc. No. EF419976. Mar. 14, 2007.
Higgins, K.L. et al. Genbank Acc. No. DQ979745. Nov. 21, 2006.
Higgins, K.L. et al. Genbank Acc. No. DQ979778, Nov. 21, 2006.
Higgins, K.L. et al. Genbank Acc. No. DQ979545, Nov. 21, 2006.
Findlay, J.A. et al. "Insect toxins from spruce endophytes". Can. J. Chem. 2003. vol. 81, No. 4, pp. 284-292, ISSN:1480-3291.
Clark, C.L. et al. "Toxicity of conifer needle endophytes to spruce budworm". Mycol. Res. vol. 94, No. 4, pp. 508-512, ISSN:0953-7562, 1989.
Ganley, R.J., et al.; "A community of unknown, endophytic fungi in western white pine", PNAS, vol. 101, No. 27, Jul. 6, 2004, pp. 10107-10112.
Azevedo, J.L. et al.; "Endophytic microorganisms: a review on insect control and recent advances on tropical plants". EJB Electronic Journal of Biotechnology. Apr. 15, 2000, vol. 3, No. 1, pp. 40-65.
Schulz, B. et al.; "The endophytic continuum". Mycol Res. Jun. 2005, vol. 109, No. 6, pp. 661-686.
Berube, J.; "Fungal Endophytes: unsuspected potential" Branching Out, Jul. 16, 2007, modified Sep. 4, 2007, No. 34.
"*Phialocephala scopiformis* strain CBS 468.94 16S ribosomal RNA gene, partial sequence; internal transcribed spacer 1, 5.8S ribosomal RNA gene and internal transcribed spacer 2, complete sequence; and 28S ribosomal RNA gene, partial sequence.", Apr. 11, 2002, Database EMBL, retrieved from EBI. Accession No. EMBL: AF486126.
"*Ascomycete* sp. HK-S178 ITS1, 5.8S rNA gene and ITS2, isolate S178", Sep. 5, 2005, Database EMBL, retrieved from EBI. Accession No. EMBL: AM084517.
Ganley, R.J. et al., "Endophyte-mediated resistance against white pine blister rust in Pinus monticola", Forest Ecology and Management, 2008, 255: 2751-2760.
Latch, G.C.M. and Christensen M.J., "Artificial infection of grasses with endophytes", Ann. appl. Biol., 1985, 107: 17-24.
Schardl, C.L., "*Epichloe* Species: Fungal Symbionts of Grasses", Annu. Rev. Phytopathol., 1996, 34: 109-30.
Sumarah, M.W., "Spread and persistence of a rugulosin-producing endophyte in Picea glauca seedlings", Mycol. Res., 2008, 112: 731-736.
Wille, P. et al., "Mixed inoculation alters infection success of strains of the endophyte *Epichloe bromicola* on its grass host Bromus erectus", Proc. R. Soc. Lond. B, 2002, 269: 397-402.

Wagner, Bruce L. et al., Colonization of Corn, *Zea mays*, by the Entomopathogenic Fungus *Beauveria bassiana*. Applied and Environmental Microbiology, Aug. 2000, vol. 66, No. 8, p. 3468-3473.
Findlay, John A., et al. Novel Diterpenoid Insect Toxins from a Conifer Endophyte. Journal of Natural Products. vol. 58, No. 2, pp. 197-200, Feb. 1995.
Jumpponen, Ari, et al. Mycorrhizal functioning of Phialocephala fortinii with Pinus contorta on glacier forefront soil: interactions with soil nitrogen and organic matter. Mycorrhiza 1998, 7: 261-265.
Clark, Catherine L. et al., Toxicity of conifer needle endophyte to spruce budworm. Mycological Research 93 (4):508-512, 1989 (abstract only).
Berube, J. A., et al. Endophytic Fungal Flora from Eastern White Pine Needles and Apple Tree Leaves as a Means of Biological Control for White Pine Blister Rust. Proceedings of the X International Symposium on Biological Control of Weeds, 2000, Session 3 abstracts, p. 241.
Breen J. et al. Studies in the Biochemistry of Micro-organisms. Rugulosin, a Crystalline Colouring Matter of Penicillium Rugulosum. Department of Biochemistry, London School of Hygiene and Tropical Medicine, University of London, Feb. 10, 1955, pp. 618-626.
Hocking, D.; "Pythium Intermedium, a newly recognized pathogen of coniferous seedlings in Canada" Can. Plant. Dis. Surv., Dec. 1970, vol. 60, No. 4, pp. 121-123.
Frasz, Samantha Leigh et al. (2014) Distribution of the foliar fungal endophyte Phialocephala scopiformis and its toxin in the crown of a mature white spruce tree as revealed by chemical and qPCR analyses. Can J Forest Res 44:1138-1143.
Frasz, Samantha Leigh (2014) The development and comparison of quantitative PCR assays and enzyme-linked immunosorbent assays as rapid detection methods for specific foliar endophytes. MSc thesis, Department of Biology, Carleton University, Ottawa, Ontario.
Pirtilla, Anna Maria and Sorvari, Seppo. Prospects and Applications for Plant Associated Microbes, A laboratory manual: Part B Fungi (Google eBook). Dec. 15, 2014. p. 217.
Zhang, Wen et al. Diversity of Antimicrobial Pyrenophorol Derivatives from an Endophytic Fungos, *Phoma* sp. European Journal of Organic Chemistry. vol. 2008, Issue 25. (Abstract provided).
Sumarah M.W., et al., 2008. Characterization of polyketide metabolites from foliar endophytes of Picea glauca. J. Nat. Prod. 71, 1393-1398. (Abstract provided).
Sumarah, M.W. and Miller, J.D., 2009. Anti-insect secondary metabolites from fungal endophytes of conifer trees . Nat. Prod. Commun. 4, 1497-1504. (Abstract provided).
Sumarah, Mark W., et al. Secondary metabolites from anti-insect extracts of endophytic fungi isolated from Picea rubems. 2010. Phytochemistry 71, 760-765.
Sumarah, Mark W. et al. Antifungal metabolites from fungal endophytes of Pinus Strobus. 2011 Phytochemistry 72 (14), 1833-1837.
Richardson, Susan N., et al. Griseofulvin-producing Xylaria endophytes of Pinus strobus and Vaccinium angustifolium: evidence for a conifer-understory species endophyte ecology. Fungal Ecology, 11(2014) 107-113.
Miller, J. David et al. Horizontal transmission of the Picea glauca foliar endophyte Phialocephala scopiformis CBS 120377. Fungal Ecology, 2 (2009), 98-101.
Aime, M. Catherine et al. Pucciniomycotina. Systematics and Evolution, 2nd Edition. They Mycota VII Part A., 2014, pp. 271-294.

\* cited by examiner

```
                        SEQUENCE LISTING

<160> NUMBER OF SEQ ID NOS: 7

<210> SEQ ID NO 1
<211> LENGTH: 20
<212> TYPE: DNA
<213> ORGANISM: Unknown
<220> FEATURE:
<223> OTHER INFORMATION: Fungus

<400> SEQUENCE: 1
tcctccgctt attgatatgc                                               20

<210> SEQ ID NO 2
<211> LENGTH: 22
<212> TYPE: DNA
<213> ORGANISM: Unknown
<220> FEATURE:
<223> OTHER INFORMATION: Fungus

<400> SEQUENCE: 2
cttggtcatt tagaggaagt aa                                            22

<210> SEQ ID NO 3
<211> LENGTH: 133
<212> TYPE: DNA
<213> ORGANISM: Unknown
<220> FEATURE:
<223> OTHER INFORMATION: Fungus

<400> SEQUENCE: 3
cattaaagaa tacatggcct tcgggtccta ttctcaccct ttgtttacca aaactcttgt    60
tgccttggcg cattcgtgcg ccaaaggaat caaaccttg aatctctgct gtctgagtac    120
tatataatag tta                                                      133
```

<210> SEQ ID NO 4
<211> LENGTH: 207
<212> TYPE: DNA
<213> ORGANISM: Unknown
<220> FEATURE:
<223> OTHER INFORMATION: Fungus

<400> SEQUENCE: 4

```
cattaaagaa tacatggcct tcgggcccta ttctcaccct ttgtttacca aaactcttgt    60
tgccttggcg cattcgtgcg ccaaaggaat caaacccttg aatctctgct gtctgagtac   120
tatataatag ttaaaacttt caacaacgga tctcttggtt ctggcatcga tgaagaacgc   180
agcgaaatgc aataagtaat gtgaatt                                       207
```

<210> SEQ ID NO 5
<211> LENGTH: 300
<212> TYPE: DNA
<213> ORGANISM: Unknown
<220> FEATURE:
<223> OTHER INFORMATION: Fungus

<400> SEQUENCE: 5

```
cattaaagaa tacatggcct tcgggtccta ttctcaccct ttgtttacca aaactcttgt    60
tgccttggcg cattcgtgcg ccaaaggaat caaacccttg aatctctgct gtctgagtac   120
tatataatag ttaaaacttt caacaacgga tctcttggtt ctggcatcga tgaagaacgc   180
agcgaaatgc gataagtaat gtgaattgca gaattcatga atcatcgaat ctttgaacgc   240
acattgcgcc tcctggtatt ccgggaggca tgcctgttcg agcgtcctta caaccctcaa   300
```

<210> SEQ ID NO 6
<211> LENGTH: 200
<212> TYPE: DNA
<213> ORGANISM: Unknown
<220> FEATURE:
<223> OTHER INFORMATION: Fungus

<400> SEQUENCE: 6

```
cattacaacc ctcaagctct gcttggtatt gggctcgcct cctttggcct gcctcaaaat    60
cagtggcggc acagtccgat cctcaagcgc agtaatacac gacgcttgcc ggtgaaggtt   120
gctgctccag aaaccccca caaactaaag gttgacctcg gatcaggtag ggatacccgc   180
tgaacttaag catatcaata                                               200
```

<210> SEQ ID NO 7
<211> LENGTH: 194
<212> TYPE: DNA
<213> ORGANISM: Unknown
<220> FEATURE:
<223> OTHER INFORMATION: Fungus

<400> SEQUENCE: 7

```
cattacaacc ctcaagctct gcttggtatt gggctcgcct cctttggcct gcctcaaaat    60
cagtggcggc acagtccgat cctcaagcgc agtaatacac gacgcttgcc ggtgaaggtt   120
gctgctcccg aaaccccca caaactaaag gttgaccacg gatcatgtag ggatacccgc   180
tgaacttaag cata                                                     194
```

ANTIFUNGAL METABOLITES FROM FUNGAL ENDOPHYTES OF *PINUS STROBUS*

CROSS REFERENCE TO RELATED APPLICATION

This application claims the benefit of 35 USC 119 based on the priority of U.S. Provisional Application No. 61/437,468 filed Jan. 28, 2011, which is herein incorporated by reference.

SEQUENCE LISTING

A computer readable form of the Sequence Listing "1414-146.txt" (2,636 bytes), submitted via EFS-WEB and created on Jan. 27, 2012 is herein incorporated by reference.

FIELD OF THE DISCLOSURE

The disclosure pertains to novel antifungal compounds, endophytes producing the compounds and methods of colonizing a white pine seedling with the endophyte and/or producing a white seedling with increased tolerance to a pest.

BACKGROUND OF THE DISCLOSURE

Extracts of foliar fungal endophytes of *Picea glauca* and *P. rubens* (white and red spruce) have been shown to be antifungal and toxic to insects when incorporated into diets (Sumarah et al., 2008b, 2010; Sumarah and Miller, 2009). It has been demonstrated that seedlings can be inoculated with these endophytes and that their metabolites accumulate in the needles, providing the tree with tolerance against spruce budworm (Miller et al., 2008; Sumarah et al., 2008a). *Cronartium ribicola* (white pine blister rust) is an introduced disease found in all five needle pines in North America. This disease has caused massive economic loss especially in eastern white pine because of the broad range of this species. It has affected *Pinus monticola* (western white pine) to the point where it is no longer a viable commercial species in many regions of British Columbia, Canada. Natural populations of *Pinus* are highly susceptible to this disease. After these experiments were initiated, various species of *Pinus* have been shown to harbour endophytes (Ganley et al., 2008).

SUMMARY OF THE DISCLOSURE

The disclosure provides compounds and isolated toxigenic endophytes producing one or more of said compounds. The toxigenic endophytes were isolated from *Pinus strobus*, eastern white pine, and can be used to inoculate white pine seedlings during the susceptible time window to produce a toxigenic endophyte colonized white pine seedling or tree.

In an embodiment of the disclosure, there is included a compound of the formula (I)

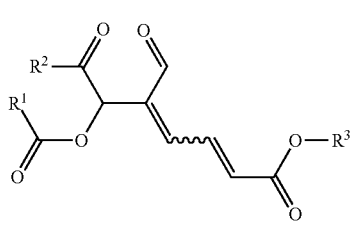

(I)

wherein $R^1$ is $(C_{1-6})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, $R^2$ are independently or simultaneously $(C_{1-6})$-alkyl, $(C_{2-6})$-alkenyl, $(C_{2-6})$-alkynyl, $(C_{3-6})$-cycloalkyl or —O—$(C_{1-6})$-alkyl, all of which are optionally substituted between one and five times with halo, $(C_{1-3})$-alkyl or fluoro-substituted-$(C_{1-3})$-alkyl, $R^3$ is H, $(C_{1-6})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, in all their stereoisomeric forms and mixtures thereof in any ratio, and their physiologically tolerable salts.

In another embodiment, there is further included a compound of the formula (II)

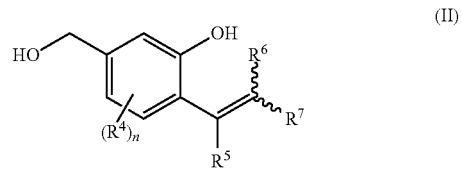

(II)

wherein $R^4$ is independently or simultaneously H, halo, OH, $(C_{1-6})$-alkyl, $(C_{2-6})$-alkenyl, $(C_{2-6})$-alkynyl, or —O—$(C_{1-4})$-alkyl, $R^5$ and $R^6$ are independently or simultaneously H, $(C_{1-4})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, $R^7$ is $(C_{1-10})$-alkyl, $(C_{2-10})$-alkenyl, $(C_{2-10})$-alkynyl, or $(C_{3-6})$-cycloalkyl, all of which are optionally substituted between one and five times with halo, $(C_{1-3})$-alkyl or fluoro-substituted-$(C_{1-3})$-alkyl, and n is an integer between 0 and 3, in all their stereoisomeric forms and mixtures thereof in any ratio, and their physiologically tolerable salts.

In another embodiment of the disclosure, there is also included a natural product extract comprising compounds of the formula (I), (II), a compound of the formula (III)

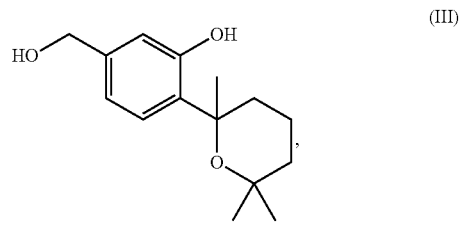 [SMILES: CC1(C)CCCC(C)(c2ccc(CO)cc2O)O1]

(III)

and compounds of the formulae (IV), (V) and (VI)

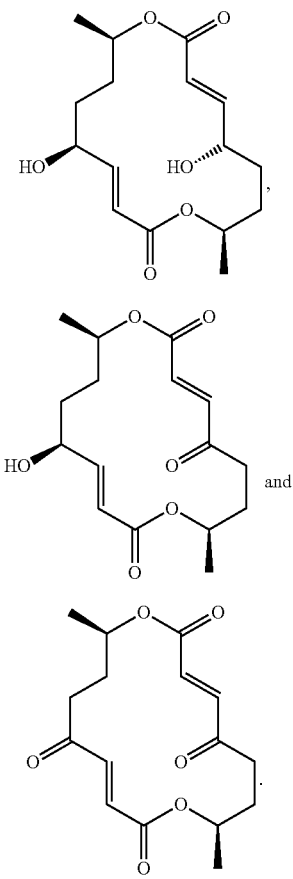

In another aspect, the disclosure includes a method of colonizing white pine seedlings with one or more toxigenic endophytes comprising inoculating one or more white pine seedlings or one or more white pine seeds with a composition and/or carrier comprising one or more toxigenic endophytes during a susceptible time window when the one or more white pine seedlings or the one or more white pine seeds are susceptible to colonization by the toxigenic endophyte, under conditions wherein at least one of the toxigenic endophytes colonizesone or more seedlings and produces a compound selected from a compound of the formula (I), (II), (III), (IV), (V) and/or (VI).

In another aspect, the disclosure includes a method of making colonized white pine seeds comprising inoculating one or more white pine seeds with a composition comprising one or more toxigenic endophytes during a susceptible time window when the one or more white pine seeds are susceptible to colonization by the toxigenic endophyte under conditions wherein at least one of the toxigenic endophytes colonizes one or more seeds and produces a compound selected from a compound of the formula (I), (II), (III), (IV), (V) and/or (VI).

In another embodiment, the method further comprises culturing the white pine seedling or white pine seed after inoculation.

In another aspect the disclosure includes a method of colonizing white pine seedlings with one or more toxigenic endophytes comprising inoculating one or more white pine seedlings with a composition and/or carrier comprising one or more toxigenic endophytes during a susceptible time window when the white pine seedlings are susceptible to colonization by the toxigenic endophyte, and culturing the white pine seedlings, under conditions wherein at least one of the toxigenic endophytes colonizes one or more seedlings and produces a compound selected from a compound of the formula (I), (II), (III), (IV), (V) and/or (VI).

In an embodiment, the one or more seedlings comprises a crop of seedlings.

In an embodiment, the seedling is an eastern white pine.

In an embodiment, the toxigenic endophyte produces one or more of preferably selected from pyrenophorol, dihydropyrenophorin and pyrenophorin.

In an embodiment, one of the one or more endophytes is an endophyte of the *Lophodermium* species that produces a compound selected from a compound of the formula (I), (II), (III), (IV), (V) and/or (VI), optionally a strain having all of the identifying characteristics of the strain deposited under the accession number CBS 127939; an endophyte comprising SEQ ID NO:3, and/or an endophyte comprising an Internal Transcribed Spacer (ITS) region having at least 99% sequence identity to SEQ ID NO:3.

In yet another embodiment, the one or more endophytes is selected from the group:
a) a strain producing a compound selected from a compound of the formula (I), (II), (III), (IV), (V) and/or (VI),
b) a strain having all of the identifying characteristics of the strain deposited under the Accession number CBS 127938, CBS 127940, CBS 127941, or CBS 127942;
c) an endophyte comprising any one of SEQ ID NO: 4 to 7; and/or
d) an endophyte comprising an Internal Transcribed Spacer (ITS) region having at least 99% sequence identity to any one of the sequences in b).

Another aspect includes an isolated toxigenic endophyte that produces a compound of the formula (I), (II), (III), (IV), (V) and/or (VI), preferably comprising a sequence selected from the group consisting of SEQ ID NOS: 3-7.

In an embodiment, the isolated toxigenic endophyte is selected from a strain having all of the identifying characteristics of a strain deposited under the Accession numbers CBS 127938, CBS 127939, CBS 127940, CBS 127941 and CBS 127942.

A further aspect includes a white pine seedling or tree colonized by an isolated toxigenic endophyte prepared by a method described herein.

Yet a further aspect includes an inoculum composition comprising an isolated toxigenic endophyte.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the disclosure will now be discussed in relation to the drawings in which.

DETAILED DESCRIPTION OF THE DISCLOSURE

Figure 1:
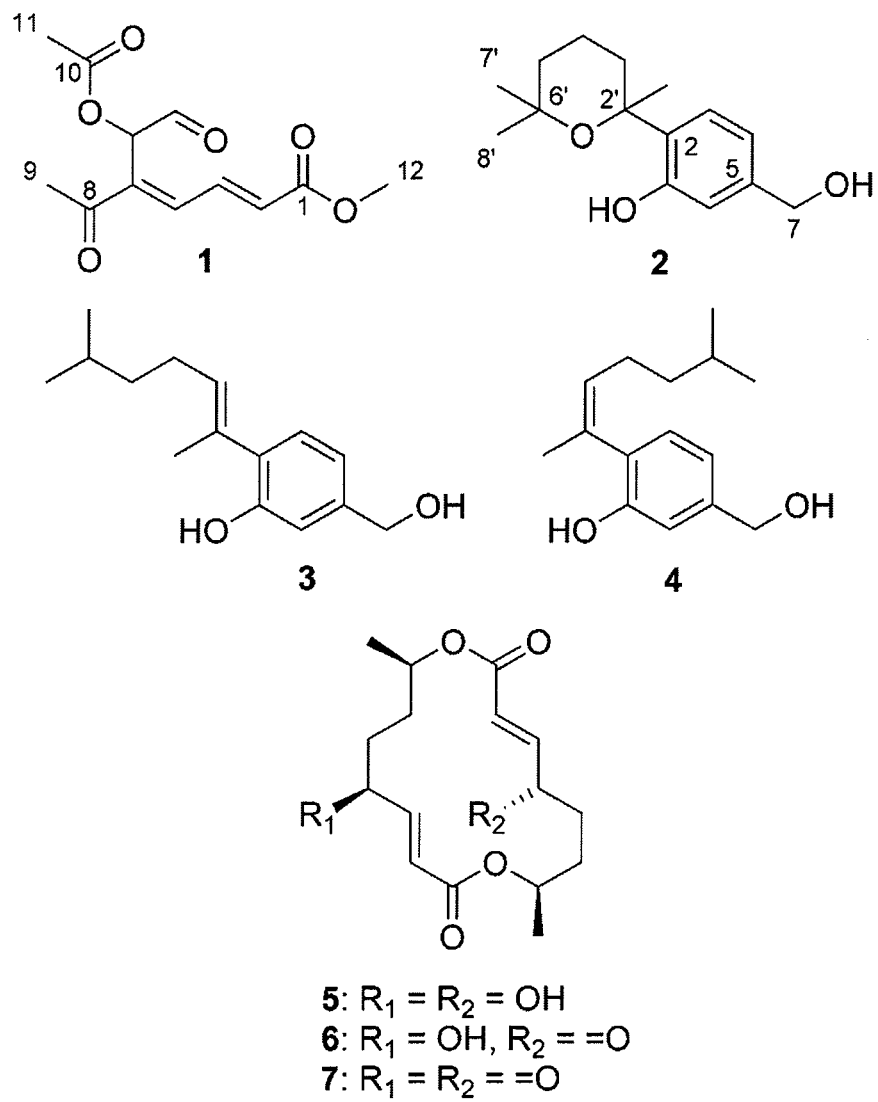
FIG. 1. Identified endophyte compounds 1 to 7.
Figure 2:
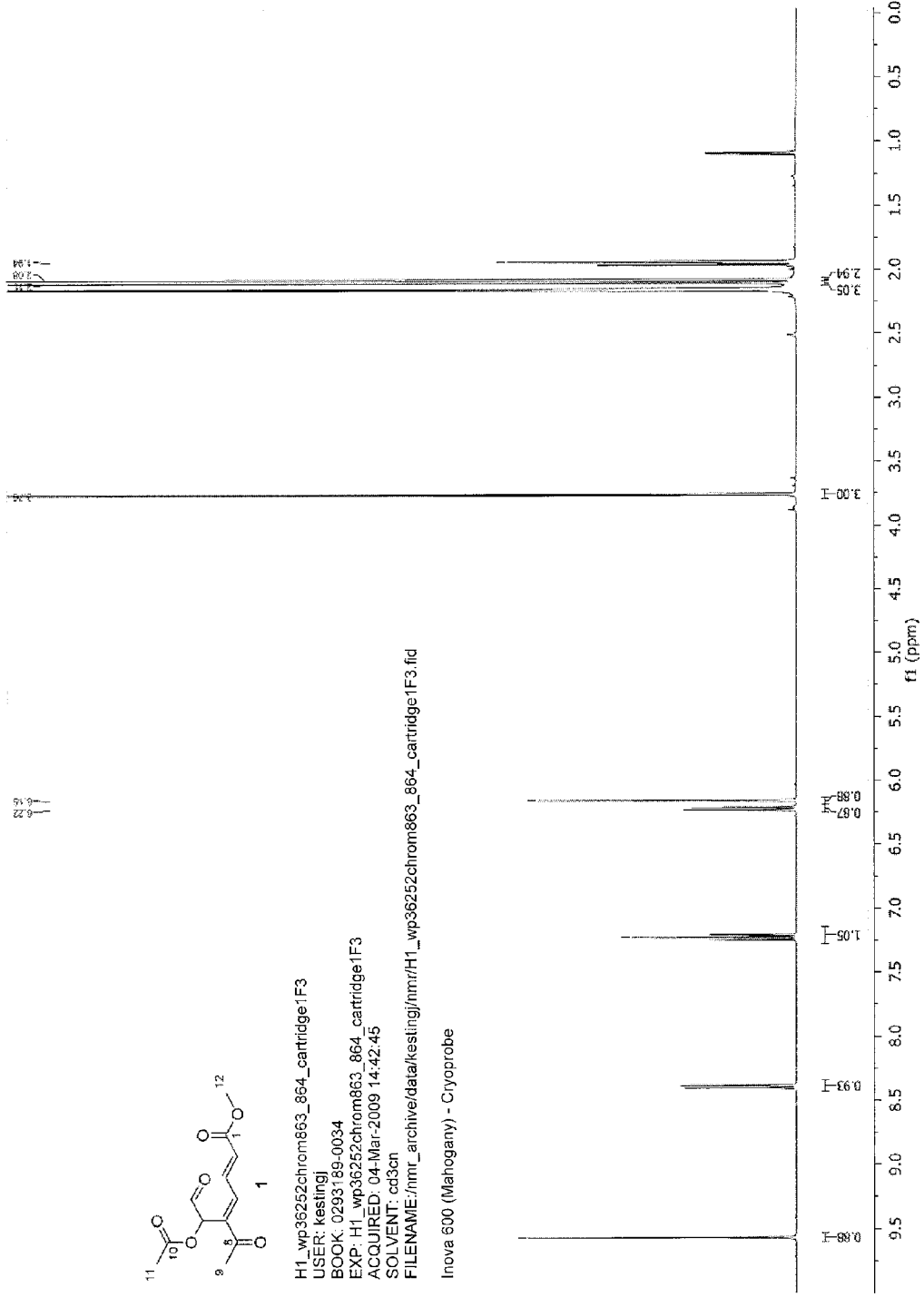
FIG. 2. $^1$H spectrum of 1 (599.92 MHz, CD$_3$CN).
Figure 3:
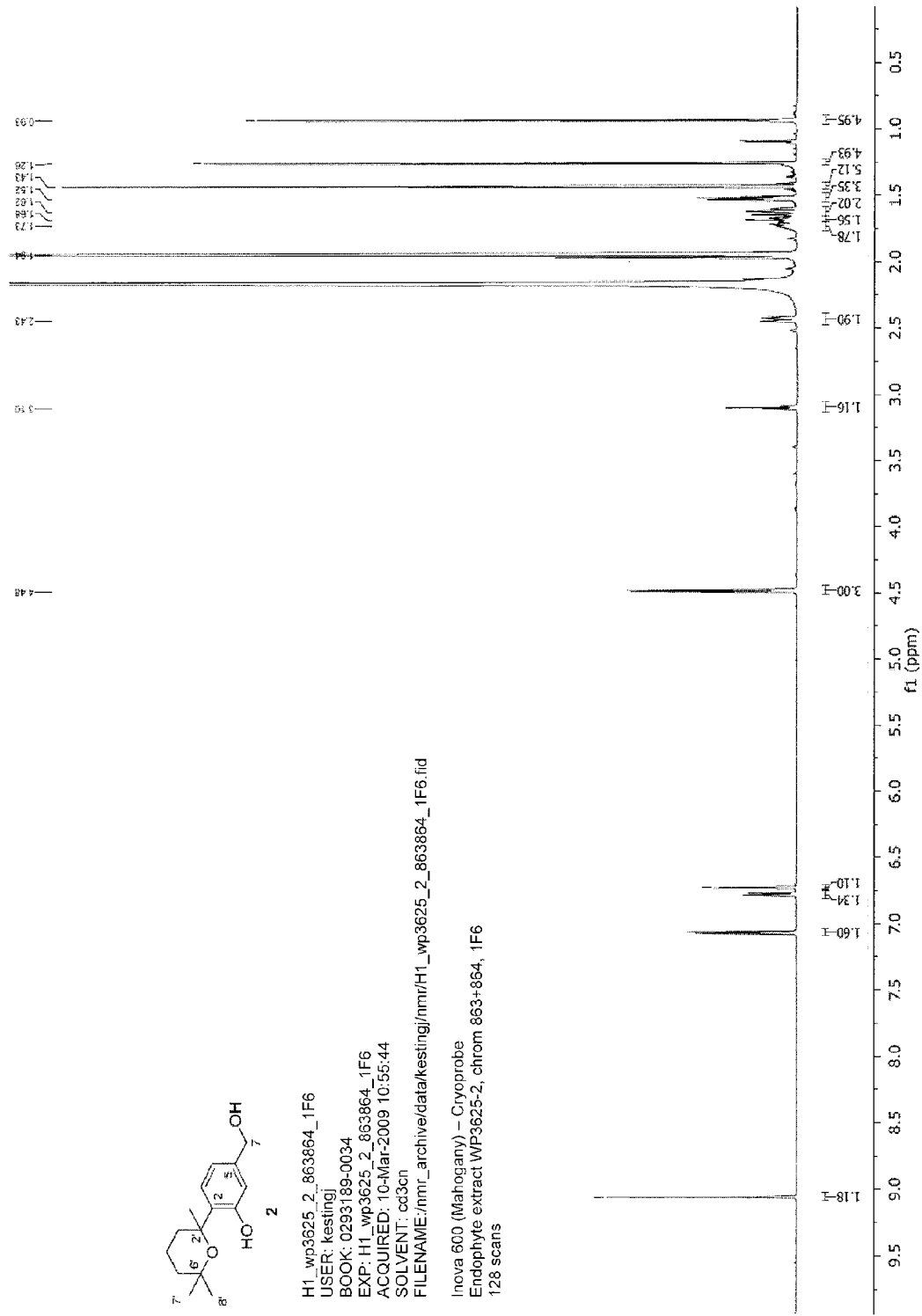
FIG. 3. $^1$H spectrum of 2 (599.92 MHz, CD$_3$CN).
Figure 4:
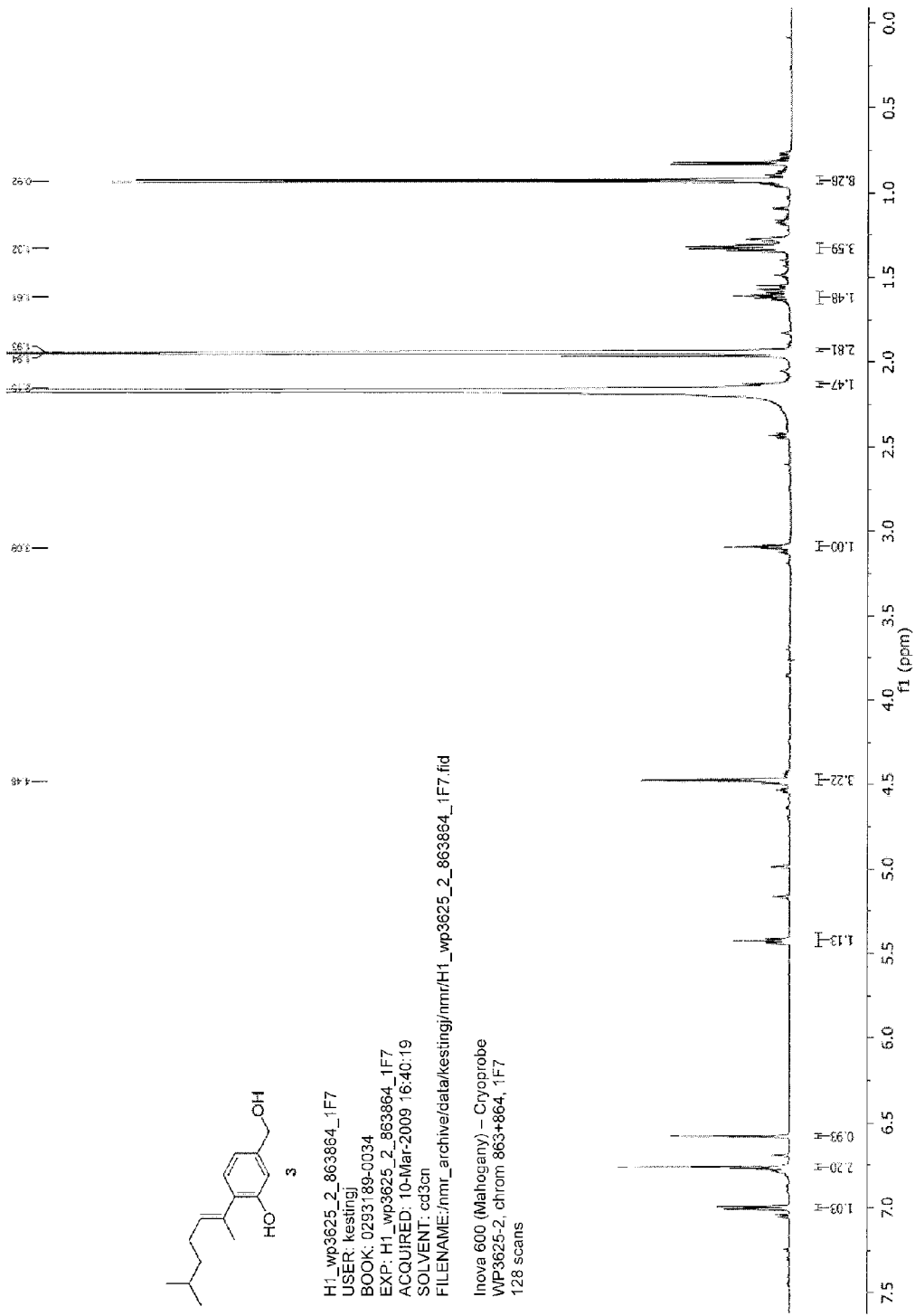
FIG. 4. $^1$H spectrum of 3 (599.92 MHz, CD$_3$CN).
Figure 5:
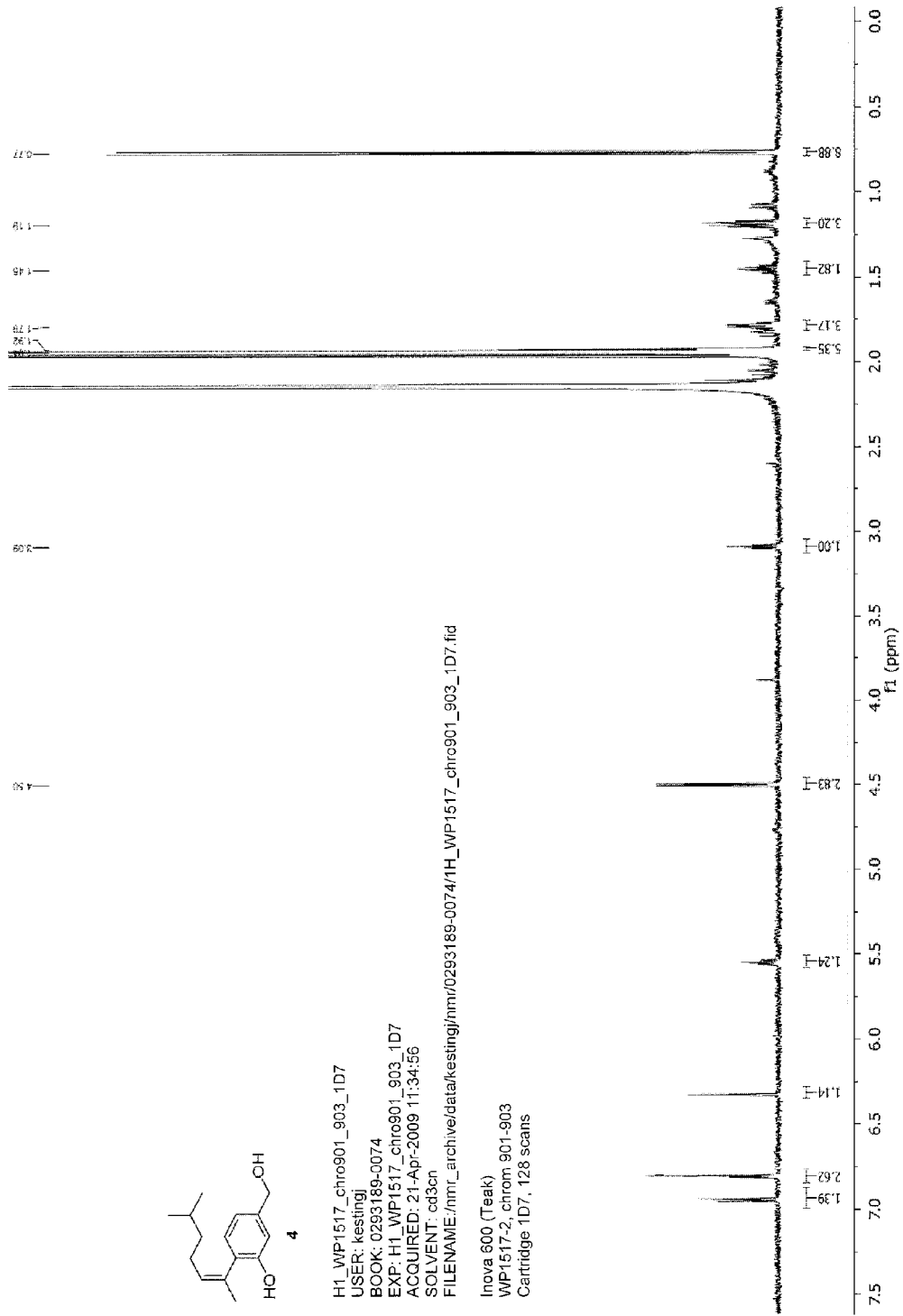
FIG. 5. $^1$H spectrum of 4 (599.92 MHz, CD$_3$CN).
Figure 6:
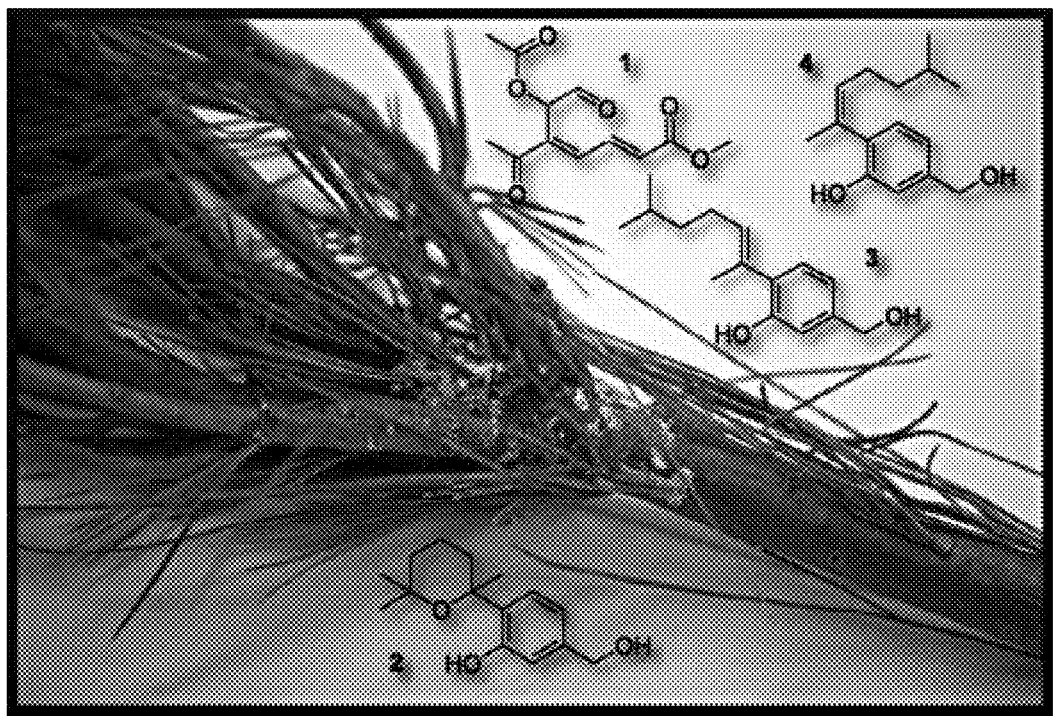
FIG. 6. The screening of fungal endophytes isolated from *Pinus strobus* needles resulted in the discovery of three new compounds (1, 3 and 4), a new natural product (2) and three known antifungals (5-7). Compounds 1, 2 and 5 showed antifungal activity against *Saccharomyces cerevisae* and *Microbotryum violaceum*.

A number of fungal endophytes were isolated from *Pinus strobus* needles, which were determined to produce antifungal compounds. The screening of these fungal endophytes isolated from *Pinus strobus* needles resulted in the discovery of three new compounds (1, 3 and 4), a new natural product (2) and three known antifungals (5-7). Compounds 1, 2 and 5 showed antifungal activity against *Saccharomyces cerevisae* and *Microbotryum violaceum*.

Accordingly the disclosure provides antifungal compounds and novel isolated toxigenic endophyte strains as well as provides methods for preparing a white pine seedling with increased tolerance to a pest.

(I) Definitions

The term "$C_{1-p}$alkyl" as used herein means straight and/or branched chain, saturated alkyl groups containing from one to "p" carbon atoms and includes (depending on the identity of) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{2-r}$alkenyl" as used herein means straight and/or branched chain, unsaturated alkyl groups containing from 2 to "r" carbon atoms and one or more, suitably one to five, more suitably one to three double bonds, and includes (depending on the identity of n), ethenyl, prop-1-enyl, prop-2-enyl, isopropenyl, but-1-enyl, but-2-enyl, but-3-enyl, isobutenyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable r is an integer representing the largest number of carbon atoms in the alkenyl radical.

The term "$C_{2-s}$alkynyl" as used herein means straight and/or branched chain, unsaturated alkyl groups containing from 2 to "s" carbon atoms and one or more, suitably one to five, more suitably one to three triple bonds, and includes (depending on the identity of s), ethynyl, propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl; 1,4-pentadiynyl, 3-methylpent-1-ynyl, 4-methylpent-2-ynyl, 1-hexynyl and the like, where the variable s is an integer representing the largest number of carbon atoms in the alkynyl radical.

The term "$(C_{3-6})$-cycloalkyl" as used herein refers to cyclic alkyl groups containing between 3 and 6 carbon atoms, and includes cyclopropyl, cyclobutyl, cyclopentyl and cyclohexyl.

The term "fluoro-substituted" with respect to any specified group as used herein means that the one or more, including all, of the hydrogen atoms in the group have been replaced with a fluorine, and includes for example, trifluoromethyl, pentafluoroethyl, fluoromethyl and the like.

The term "halo" as used herein refers to halogen atoms or halogen groups, and includes fluoro, chloro, bromo and iodo.

The term "white pine" as used herein means any plant of the species *Pinus strobus* having needles in clusters of five, also referred to as eastern white pine, as well as plants of the species *Pinus monicola* referred to as western white pine, and closely related species or a part thereof including a seed, needle, tissue or isolated cell culture derived from a part thereof.

The term "culturing a white pine seedling or white pine seed" as used herein means providing suitable conditions e.g. light, water and nutrients, to allow the white pine seedling to grow or in the case of a white pine seed, to germinate and grow. Similarly, "culturing a toxigenic endophyte" means providing suitable conditions e.g. nutrients and temperature to allow the endophyte to multiply.

The term "seedling" as used herein means a post-germination plant and includes a plant grown in a nursery production facility, prior to final planting and comprises the period of seedling development from post-germination to about 16 weeks post-germination.

The term "plant" as used herein means a seedling, shrub, hedge or tree including a tree hedged for the production of rooted cuttings.

The term "colonization" as used herein means the persistence of an inoculated endophyte in a conifer plant wherein the conifer hosts the endophyte and the endophyte persists (e.g. by replication) in sufficient quantity to be detected in any assay, for example, in an antibody detection assay using an antibody directed against the endophyte and/or an assay for detecting an endophyte toxin derivative and/or persists in sufficient quantity to confer pest resistance to the host. With respect to a seed, colonization means the endophyte persists with a seedling grown from the seed.

The term "pest" as used herein means any organism that may cause injury to a white pine plant including any needle pathogen and comprises insects, insect larvae, and fungal pathogens (e.g. insect and fungal pests).

The term "fungal pest" as used herein include *Cronartium ribicola* that causes white pine blister rust and other pine needle rusts, particularly when referring to white pine fungal pests. Fungal pests also include for example *Microbotryum violaceum* species, as well as yeasts such as *Saccharomyces cerevisae*

The term "pine needle rust" as used herein refers to fungal infections that induce needle rust, characterized for example by white to orange colored bladder-like blisters that are produced on the needles, and includes species that induce white pine blister rust, and *Microbotryum violaceum*.

The term "toxigenic" as used herein means toxic to a pest such as a conifer pest. "Toxigenic" includes anti-insectan and antifungal toxicity.

The term "isolated toxigenic endophyte" as used herein means an isolated endophyte strain, incluidng spores, that produces a toxin compound (and/or one or more toxin compounds) that is/are toxic to a pest, that is able to colonize a white pine conifer seedling and/or white pine conifer seed and produce a toxin compound in the colonized plant. For example, the isolated toxigenic endophytes can be isolated from a white pine needle and/or seed and/or derived from such an isolated toxigenic endophyte. The toxin compound produced by the toxigenic endophyte confers increased pest tolerance to the white pine by controlling, reducing, or preventing colonization by the pest and/or damage caused by the pest for example by killing the pest and/or stunting pest growth, infection rate and/or activity in the endophyte-colonized white pine plant compared to a control uninoculated and/or non-colonized but otherwise equivalent white pine plant.

The term "toxin compound" as used herein means a compound or compounds of the formula (I), (II), (III), (IV), (V), and/or (VI) that confer increased fungal pest tolerance to a white pine, thereby controlling, reducing, mitigating, preventing or repelling fungal pests and/or fungal pest infection rate or growth and/or fungal pest damage. In addition, the toxin compound can reduce, mitigate, prevent or repel other pests and/or pest infection rate growth and/or pest damage, such as insects. Included for example, are compounds produced by toxigenic endophytes described in Table 1. The ability of a toxin compound to control, reduce, mitigate, prevent or repel a pest and/or pest infection or growth and/or pest damage can be assessed for example, in vitro using a pest toxicity assay, which assesses pest growth such as fungal growth in the presence and absence of the test compound.

The term "increase" related to a function or activity, such as increased pest tolerance, means any detectable or measurable increase in the function or activity when compared to otherwise same conditions, except for a condition or parameter of interest, or alternatively, as compared to another condition.

The term "inhibit", "retard" or "reduce" a function or activity, such as fungal growth, means any detectable or measurable reduction in the function or activity when compared to otherwise same conditions, except for a condition or parameter of interest, or alternatively, as compared to another condition.

The term "toxicity" as used herein with respect to the effect of a toxin compound or toxigenic endophyte strain on a pest means inhibited or reduced growth and/or pest death in the presence of the toxin compound or toxigenic endophyte compared to a control. For example, where toxicity is assessed using a disc diffusion assay, which uses a disc comprising a compound, which is placed on a microbial lawn, the compound is a toxic compound if it results in a zone of clearing around the disc.

The term "pest growth" as used herein includes infection rate e.g. numbers of needles and/or trees colonized in a given area, and/or pest growth rate.

The term "sufficient or effective concentration to reduce pest growth and/or infection rate compared to pest growth or infection rate in a non-inoculated white pine seedling" as used herein means the amount that shows a statistically-significant reduction in pest numbers (e.g. microbial population) and/or in pest growth and/or infection rate. Such a reduction is readily determinable, for example, in a pest assay such as a disc diffusion assay or in vivo pest toxicity assays using, a toxigenic endophyte colonized seedling. The amount will vary for example according to the endophyte species, the concentration of toxin compound and the nature of toxin compound produced.

The "susceptible time window" as used herein for a white pine seedling comprises the period post germination during sustained elongation of the seedling shoot apex when the number of "intermediately developed" and "juvenile" needles is greater than the number of needles that are completely developed and mature and the cuticle is not fully formed and the susceptible time window for the white pine seed is during seed stratification. "Susceptible" is used interchangeably with "receptive" herein. For a seedling, the start of the susceptible time period is after the germination processes are largely completed. These include the time after the seed coat cracks and the radicle emerges. The radicle and hypocotyl and cotylyedons elongate rapidly to the point when the base of the cotyledon begins to elongate. During the period circumscribed by seedling heights for example >10 and/or <40 mm, the shoot apex, needle primordial and subtending internodes are initiated, expand and develop rapidly. The rudimentary needles and internodes become completely differentiated including formation of the cuticle and mesophyll. The critical period of successful inoculation is related to the percentage of needles of intermediate development versus complete development in which the cuticle is fully formed. Also wax development occurs within the cuticle and may be referred to as cuticular wax as well as on the surface of the cuticle which may be referred to as epicuticular wax. Cuticular wax may function to provide a waterproof quality from the needle surface. Without wishing to be bound by theory, it is believed that the upper time limit of the period during which the post-germination seedlings may be non-invasively inoculated corresponds to the formation of wax on and/or in the seedling that impairs inoculation. For example, the susceptible time window comprises a period where greater than 10% of inoculated seedlings or seeds are colonized using the methods disclosed herein.

The term "seed stratification" as used herein means a process of artificially or naturally interrupting a seed's embryonic dormancy so that the seed can germinate and embryonic dormancy typically comprises the period of time from taking seed from cold storage to sowing seed. "Embryonic seed dormancy" is optionally interrupted for white spruce by soaking the seed in water overnight and exposing the drained seed to temperatures of approximately 2-6° C. for approximately 2 weeks. The term "germination" as used herein means the cracking of the seed coat and growth of a seedling from a seed.

The term "inoculation" and/or "inoculating" as used herein means providing an endophyte for example in a composition (e.g. inoculum composition) in a manner that permits the provided endophyte to colonize the seedling or seed or using a carrier to a white pine seedling in a manner that permits the provided endophyte to colonize the seedling. For example, the inoculation can comprise contacting a seedling or seed with inoculum, and incubating or culturing the seedling or seed under conditions that permit the inoculum to remain in contact with the seedling or seed for at least 1 hour, 2 hours, 3 hours, 4 hours, 5 hours, 6 hours, 7 hours, 8 hours, 9 hours, 10 hours or at least 12 hours. Where the inoculation is of a seedling, the inoculation can comprise contacting the seedling with inoculum and incubating or culturing the seedling under conditions that permit liquid droplets of the inoculum to persist for at least 1 hour, 2 hours, 3 hours, 4 hours, 5 hours, 6 hours, 7 hours, 8 hours, 9 hours, 10 hours or at least 12 hours. The "conditions that permit" can comprise for example repeated application e.g. repeated spraying or application of an inoculum volume sufficient to permit liquid droplets to persist on the seedling. Alternatively, a carrier can be provided that comprises the toxigenic endophyte and is placed in contact with the seedling (and/or the seedling growth medium) for a sufficient period of time to permit colonization. Where the method comprises inoculating seeds, the inoculation can comprise contacting a seed with inoculum (e.g soaking) and incubating or culturing the seed for at least the previously stated time. The inoculum composition is optionally a laboratory prepared composition comprising a toxigenic endophyte. The carrier can be plant part (e.g. case needles) that is colonized by a toxigenic endophyte and/or which is coated or otherwise impregnated with a composition comprising one or more toxigenic endophytes.

The term an "inoculum composition" and/or "inoculum" as used herein means a composition comprising one or more toxigenic endophytes and a diluent and in reference to inoculating means a composition wherein the toxigenic endophyte is present in an effective amount to colonize a white pine seedling or white pine seed.

The term "effective amount" as used herein refers to an amount effective at concentrations and for periods of time necessary to achieve the desired result, for example an amount sufficient to confer, for example increased pest tolerance.

A "propagule" as referred herein means an infective fungal cell. A person skilled in the art will recognize that the quantity of toxigenic endophyte inoculated may vary with environmental and other factors. For example, if inoculation of white pine seedlings is performed during environmental conditions such as low temperature, that are not favourable to endophyte inoculation, the quantity of toxigenic endophyte is optionally increased. Similarly, repeated inoculations are optionally used if seedlings are exposed to various environmental conditions, such as heavy rainfall where the inoculum composition is diluted or washed away.

The term "contacting" is used interchangeably with "applying".

The term "intact seedling" as used herein refers to a seedling wherein the seedling remains unwounded prior to, or during, contact with the inoculum composition. More specifically, the stem of an intact seedling is not pierced or wounded prior to, or during, contact with the inoculum composition. An inoculum composition is optionally applied to an intact seedling by spraying the intact seedling with the inoculum composition. The use of intact seedlings is very advantageous because it eliminates the plant wounding step and facilitates rapid inoculation, providing very important time savings in a high-throughput conifer nursery setting.

The term "crop" as used herein refers to at least a hundred, hundreds, or at least a thousand seedlings, for example tens of thousands of seedlings, including hundreds of thousands of seedlings or more.

The term "juvenile needle" as used herein refers to a type of needle typically present in seedlings during a juvenile phase. Mature needles are produced at later stages of seedling development and are structurally different compared to juvenile needles.

The term "intermediately developed needle" as used herein the stage of needle development of a mature needle, for example wherein the cuticle is not fully formed.

The term "sequence that has substantial sequence homology" means those nucleic acid sequences which have slight or inconsequential sequence variations from the sequences in (a) or (b). The variations may be attributable to local mutations or structural modifications. Nucleic acid sequences having substantial homology include nucleic acid sequences having at least 65%, more preferably at least 85%, and more preferably 90-95% identity with the nucleic acid sequences of SEQ ID NO:3-7.

The term "probe" as used herein refers to a nucleic acid sequence that will hybridize to a nucleic acid target sequence. In an example, the probe hybridizes to DNA of a candidate toxigenic endophyte. Specifically, in an embodiment the probe hybridizes to internal transcribed spacer (ITS) sequence of ribosomal DNA of a candidate toxigenic endophyte. The length of probe depends on the hybridization conditions and the sequences of the probe and nucleic acid target sequence. In an embodiment, the probe is at least 8, 10, 15, 20, 25, 50, 75, 100, 150, 200, 250, 400 or more nucleotides in length.

The term "isolated nucleic acid sequence" as used herein refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The term "hybridize" refers to the sequence specific non-covalent binding interaction with a complementary nucleic acid. One aspect of the invention provides an isolated nucleotide sequence, which hybridizes to a candidate toxigenic endophyte DNA. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. for 15 min may be employed. The stringency may be selected based on the conditions used in the wash step. For example, the salt concentration in the wash step can be selected from a high stringency of about 0.2×SSC at 50° C. for 15 min. In addition, the temperature in the wash step can be at high stringency conditions, at about 65° C.

By "at least moderately stringent hybridization conditions" it is meant that conditions are selected which, promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(% (G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. for 15 min. Moderately stringent hybridization conditions include a washing step in 3×SSC at 42° C. for 15 min. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

(II) Compounds Of The Disclosure

The extracts of five foliar fungal endophytes from *Pinus strobus* (eastern white pine) showed antifungal activity in disc diffusion assays. A new aliphatic polyketide and three new related sesquiterpenes were isolated and characterized. Additionally, the three known macrolides; pyrenophorol, dihydropyrenophorin and pyrenophorin were isolated and identified. Structures were elucidated by 2D NMR and LC-HRMS. The isolated compounds were tested for antifungal activity against *Saccharomyces cerevisae* and the rust *Microbotryum violaceum*.

In an embodiment of the disclosure, there is included a compound of the formula (I)

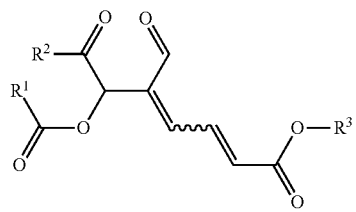

(I)

wherein
$R^1$ is $(C_{1-6})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, $R^2$ are independently or simultaneously $(C_{1-6})$-alkyl, $(C_{2-6})$-alkenyl, $(C_{2-6})$-alkynyl, $(C_{3-6})$-cycloalkyl or —O—$(C_{1-6})$-alkyl, all of which are optionally substituted between one and five times with halo, $(C_{1-3})$-alkyl or fluoro-substituted-$(C_{1-3})$-alkyl, $R^3$ is H, $(C_{1-6})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, in all their stereoisomeric forms and mixtures thereof in any ratio, and their physiologically tolerable salts.

In another embodiment, $R^1$ is $(C_{1-3})$-alkyl, $(C_{2-3})$-alkenyl, $(C_{2-3})$-alkynyl, or $(C_{5-6})$-cycloalkyl, all of which are optionally substituted. In another embodiment, $R^1$ is methyl, ethyl, propyl or isopropyl, optionally methyl. In an embodiment, $R^2$ is $(C_{1-3})$-alkyl, $(C_{2-3})$-alkenyl, $(C_{2-3})$-alkynyl, $(C_{5-6})$-cycloalkyl or —O—$(C_{1-3})$-alkyl, all of which are optionally substituted. In another embodiment, $R^2$ is methyl, ethyl, propyl or isopropyl, optionally methyl. In another embodiment, $R^3$ is H, $(C_{1-3})$-alkyl, $(C_{2-3})$-alkenyl, $(C_{2-3})$-alkynyl, or $(C_{5-6})$-cycloalkyl, all of which are optionally substituted. In another embodiment, $R^3$ is methyl, ethyl, propyl or isopropyl, optionally methyl.

In another embodiment, the compound of the formula (I) is

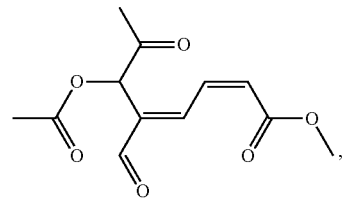 [SMILES: COC(=O)/C=C\C=C(\C=O)C(OC(C)=O)C(C)=O]

which is (2Z,4E)-methyl-6-acetoxy-5-formyl-7-oxo-octa-2,4-dienoate.

In another embodiment, there is further included a compound of the formula (II)

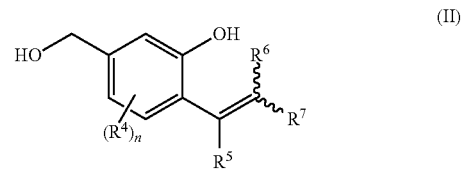

(II)

wherein
$R^4$ is independently or simultaneously H, halo, OH, $(C_{1-6})$-alkyl, $(C_{2-6})$-alkenyl, $(C_{2-6})$-alkynyl, or —O—$(C_{1-6})$-alkyl, the latter four groups being optionally substituted between one and five times with halo, $(C_{1-3})$-alkyl or fluoro-substituted-$(C_{1-3})$-alkyl, $R^5$ and $R^6$ are independently or simultaneously H, $(C_{1-6})$-alkyl, $(C_{2-6})$-alkenyl, $(C_{2-6})$-alkynyl, or $(C_{3-6})$-cycloalkyl, all of which are optionally substituted between one and five times with halo, $(C_{1-3})$-alkyl or fluoro-substituted-$(C_{1-3})$-alkyl, $R^7$ is $(C_{1-10})$-alkyl, $(C_{2-10})$-alkenyl, $(C_{2-10})$-alkynyl, or $(C_{3-6})$-cycloalkyl, all of which are optionally substituted between one and five times with halo, $(C_{1-3})$-alkyl or fluoro-substituted-$(C_{1-3})$-alkyl, and n is an integer between 0 and 3, in all their stereoisomeric forms and mixtures thereof in any ratio, and their physiologically tolerable salts.

In another embodiment, $R^4$ is independently or simultaneously H, halo, OH, $(C_{1-3})$-alkyl, $(C_{2-3})$-alkenyl, $(C_{2-3})$-alkynyl, or —O—$(C_{1-3})$-alkyl. In another embodiment, $R^4$ is independently or simultaneously H, halo, OH or $CH_3$. In an embodiment, $R^4$ is H.

In another embodiment, $R^5$ and $R^6$ are independently or simultaneously H, $(C_{1-3})$-alkyl, $(C_{2-3})$-alkenyl, $(C_{2-3})$-alkynyl, or $(C_{5-6})$-cycloalkyl. In another embodiment, $R^5$ is methyl. In an embodiment, $R^6$ is H.

In another embodiment, $R^7$ is $(C_{3-8})$-alkyl, $(C_{3-8})$-alkenyl, $(C_{3-8})$-alkynyl, or $(C_{5-6})$-cycloalkyl. In another embodiment, $R^7$ is $(C_{5-6})$-alkyl, $(C_{5-6})$-alkenyl or $(C_{5-6})$-alkynyl.

In another embodiment, the compound of the formula (II) is

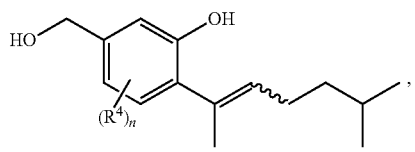

wherein $R^4$ and n are as defined above. In an embodiment, $R^4$ is H.

In another embodiment, the compound of the formula (II) is a compound of the formula (IIa) or (IIb)

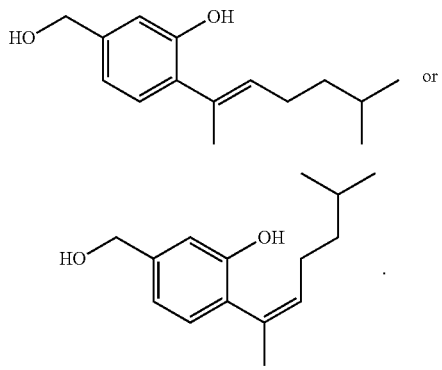

In another embodiment of the disclosure, there is also included a natural product extract comprising compounds of the formulae (I), (II) as defined above, a compound of the formula (III)

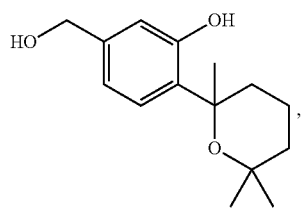

and compounds of the formulae (IV), (V) and (VI)

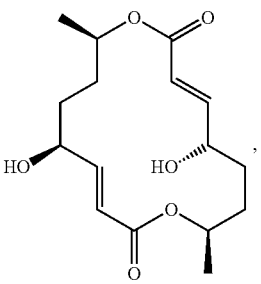

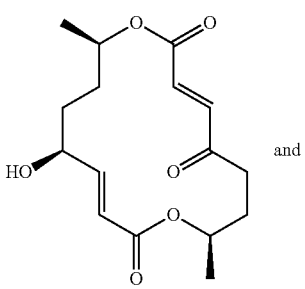

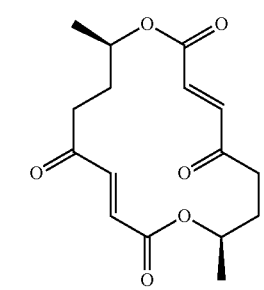

Synthetic methods for preparing the compound of the formula (III) are known, see for example, Serra S. 2000.

In another embodiment, the natural product extract comprises (2E,4Z)-methyl-6-acetoxy-5-acetyl-7-oxohepta-2,4-dienoate and compounds of the formulae (IIa), (IIb), (III), (IV), (V) and/or (VI).

The compounds can be isolated for example by culturing a toxigenic endophyte and isolating the particular compound using for example analytical methods.

In an embodiment, the compounds defined above have been demonstrated herein to be metabolites produced by toxigenic endophytes isolated from *Pinus strobus*. These are the major components of the mixture of different anti-insectan and/or anti-fungal metabolites produced by each strain. In an embodiment, the compound is a derivative or metabolite of a compound of the formula (I), (II), (III), (IV), (V) and/or (VI) thereof that is toxic.

An aspect includes a composition comprising a compound of the disclosure. In an embodiment, the composition comprises a compound of the formula (I), and/or (II) as defined above and/or combinations thereof. In an embodiment, the composition further comprises a compound of the formula (III), (IV), (V) and/or (VI) and/or combinations thereof.

In an embodiment, the composition comprises a diluent. In an embodiment, a diluent refers to any liquid or solid pharmaceutically, veterinarily, agriculturally etc. acceptable material, including carriers, which may be added to the active constituents to bring them in a suitable application or commercial form.

It is demonstrated herein that compositions comprising compounds of the formula (I) (such as (2E,4Z)-methyl-6-acetoxy-5-acetyl-7-oxohepta-2,4-dienoate), and compounds of the formulae (III) and (IV) had antifungal activity to a representative ascomycete, *S. cerevisae* and a rust (*M. violaceum*). The rust is biologically similar to white pine blister rust. Accordingly, in an embodiment, the composition is an antifungal composition comprising a compound of the formula (I), and/or (II) and/or combinations thereof. In an embodiment, the antifungal composition further comprises a compound of the formula (III), (IV), (V) and/or (VI) and/or combinations thereof. In an embodiment, the antifungal composition is for controlling growth of a fungus. In an embodiment, the fungus is a species that causes needle rust. In another embodiment, the fungus is *Cronartium ribicola*. In an embodiment the fungus is a *Microbotryum violaceum* species. In an embodiment the fungus is a yeast, such as *Saccharomyces cerevisae*.

(III) Endophytes

Disclosed herein are a number of isolated white pine toxigenic endophytes. Accordingly, an aspect of the disclosure includes an isolated toxigenic endophyte that produces a compound of the formula (I), (II), (III), (IV) and/or (III) and/or combinations thereof. In an embodiment, the isolated toxigenic endophyte alternatively and/or further produces a compound of the formula (IV), (V) and/or (VI).

The Internal Transcribed Spacer (ITS) nucleotide sequence has been determined for strains demonstrated to produce compounds that are toxigenic to fungal pest species.

Nucleic acids comprising the ITS sequences are useful as probes or to design probes to identify related and toxigenic endophytes. Accordingly, one embodiment provides a method of isolating a candidate toxigenic endophyte comprising contacting an endophyte nucleic acid, such as DNA, with a probe, the probe comprising sequences corresponding to at least 50 nucleotides of sequence selected from the group comprising SEQ ID NOS: 3-7, wherein endophytes with at least: 80%, 85%, 90%, 95%, 97%, 98% or 99% sequence identity are candidate toxigenic endophytes. In an embodiment, the method further comprises confirming toxin production, wherein and endophyte that produces a compound selected from a compound of the formula (I), (II), (III), (IV), (V) and/or (VI), is a toxigenic endophyte.

In another embodiment, the isolated toxigenic endophyte comprises a sequence selected from the group consisting of SEQ ID NOS: 3-7; a sequence comprising at least 90%, at least 91%, at least 92%, at least 93%, at least 94%, at least 95%, at least 96%, at least 97%, at least 98% or at least 99% sequence identity to a sequence selected from SEQ ID NO:3-7. Accordingly, in an embodiment, the isolated toxigenic endophyte comprises a sequence selected from the group consisting of SEQ ID NOS: 3-7; a sequence comprising at least 90%, at least 91%, at least 92%, at least 93%, at least 94%, at least 95%, at least 96%, at least 97%, at least 98% or at least 99% sequence identity to a sequence selected from SEQ ID NO:3-7 and produces a compound selected from a compound of the formula (I), (II), (III), (IV), (V) and/or (VI), Sequence analysis suggests that the five strains isolated and tested are *Lophodermium* species.

In an embodiment, the toxigenic endophyte is a *Lophodermium* species.

Representative isolated toxigenic endophyte strains have been deposited under the Accession numbers CBS 127938, CBS 127939, CBS 127940, CBS 127941 and CBS 127942. The foregoing were deposited on Sep. 29, 2010, in the Centraalbureau voor Schimmelcutures depository, Uppsalalaan 8, P.O. Box 851673508 AD Utrecht, The Netherlands. The deposits were made in accordance with the Budapest treaty.

Accordingly in an embodiment, the isolated toxigenic endophyte is a strain deposited under the Accession numbers CBS 127938, CBS 127939, CBS 127940, CBS 127941 or CBS 127942.

Another aspect of the disclosure includes a composition comprising one or more isolated toxigenic endophytes. The isolated endophytes deposited under the Accession numbers CBS 127938, CBS 127939, CBS 127940, CBS 127941 and/or CBS 127942 produce one or more toxin compounds as described herein (Table 1). Compositions comprising more than one toxigenic endophyte can comprise toxigenic endophytes with different toxin profiles. Also compositions comprising more than one toxigenic endophyte may have an advantage in inoculating different white pine genotypes. For example, in methods comprising inoculating more than one seedling such as a crop, using a composition comprising more than one toxigenic endophyte can result in a population of seedlings colonized with different endophytes. Diverse communities of endophytes can be important for durability and tolerance.

In an embodiment, the composition comprises 2 or more, 3 or more, 4 or more, or 5 toxigenic endophytes.

In an embodiment, the composition comprises a toxigenic endophyte that produces a compound of the formula (I), (II), (III), (IV), (V) and/or (VI) and/or combinations thereof. In an embodiment, the toxigenic endophyte produces a compound of the formula (I), (II), and/or (III) and/or combinations thereof.

In an embodiment, the composition comprises an endophyte having all of the identifying characteristics of a strain deposited under the Accession number CBS 127939. In an embodiment, the composition further comprises an endophyte selected from an endophyte having all of the identifying characteristics of a strain deposited under the Accession numbers CBS 127938, CBS 127940, CBS 127941 or CBS 127942.

In an embodiment, the isolated toxigenic endophyte or composition comprising one or more toxigenic endophytes is for inoculating a white pine seedling.

Another aspect of the disclosure includes an inoculum composition comprising an isolated toxigenic endophyte that produces a compound of the formula (I), (II), (III), (IV), (V) and/or (VI) and/or combinations thereof, and a diluent.

The effectiveness of the inoculum varies for example with the length of time the inoculum has been stored. Preferably, the inoculum is harvested, diluted and/or prepared the same day as the inoculation.

In an embodiment, the inoculum is freshly prepared. In an embodiment, the diluent comprises water.

Also provided is a method of preparing an inoculum composition comprising combining a diluent and an isolated toxigenic endophyte described herein, such as a toxigenic endophyte selected from a strain having all of the identifying characteristics of a strain deposited under Accession number CBS 127938, CBS 127939, CBS 127940, CBS 127941, and/or CBS 127942, grown according to a method comprising:

a) growing an initial culture such as a slant culture of the toxigenic endophyte;
b) inoculating a first liquid culture with a suspension comprising the initial culture wherein the first liquid culture is grown for approximately 2 weeks;
c) maceration of the first liquid culture using a shear force that shears the endophyte hypha; and d) inoculation of a second liquid culture with the macerated first liquid culture;

wherein the second culture is grown in a large vessel, and is aerated.

The filaments of the toxigenic endophyte are optionally sheared by a shearing means which reduces the number of dead endophytes produced compared to other maceration methods, thereby increasing the number of live toxigenic endophytes per volume inoculum and facilitating the colonization of inoculated conifer seedlings.

In another embodiment, hyphae sheared from the toxigenic endophyte, optionally sheared to provide endophyte clusters of mycelium or spores and wherein the clusters are less than 5 mm. In a further embodiment, the toxigenic endophyte is cultured to provide toxigenic endophyte clusters of mycelium or spores wherein the clusters are less than 5 mm in diameter or length, optionally less than 10 mm in diameter or length. In a further embodiment, the hyphae are sheared by rotating the culture medium at a rotation of least 200 rpm to 310 rpm.

In an embodiment, the second culture is maceration using a shear force that shears the endophyte hypha.

In an embodiment, the endophyte is grown in a stirred jar fermentation unit such that the cells are present in not larger than 5 mm clusters of mycelium or spores, are greater than 80% and preferably greater than 95% viable and greater than 80% and preferably greater than 95% infective in receptive tissue in liquid substantially free of bacteria and material concentrations of residual nutrients.

In another embodiment, toxigenic endophyte is aerated when the toxigenic endophyte is cultured. In yet another embodiment, the composition further comprises a stabilizing agent, optionally wherein the stabilizing agent comprises a carbohydrate.

In an embodiment, the second liquid culture is grown in a fermentor. In an embodiment, the inoculum composition is optionally harvested from the large vessel, which includes a fermentor, centrifuged and resuspended in a diluent. In an embodiment the diluent is sterile water.

In an embodiment, the agar slant is a malt agar slant. In another embodiment the first liquid culture is 2% malt extract and the suspension is added at 5% v/v. The shear force in an embodiment comprises shaking or rotation at 200-310 RPM. In another optional embodiment the shaking or rotation is at 220 RPM. In an embodiment, the first liquid culture is preferably incubated at 25° C. In an embodiment the first liquid culture comprises a malt extract. In another embodiment the macerated liquid culture is added to a 1-3% malt extract broth. In an embodiment, the malt extract concentration is approximately 1%. In another embodiment, the macerated liquid culture and malt extract broth are stirred at 200-310 RPM, for example stirring at 280 RPM. In another embodiment, the temperature in the large vessel which may optionally be a stirred fermentor, is 20-22° C. and is optionally 21° C. In another embodiment, the aeration is 0.05-0.15 v/v per minute and is optionally 0.1 v/v per minute. In another embodiment, the macerated liquid culture and malt extract are incubated for 6-10 days and preferably 7 days. A person skilled in the art would understand what routine adaptations would be required to grow the new toxigenic endophyte strains identified. In addition a person skilled in the art would understand that changes to sugar concentration, temperature and oxygen tension may require compensating changes in other variables. A person skilled in the art would also understand the routine experiments to further scale up the production of inoculum composition.

The inoculum composition may be diluted or concentrated. In an embodiment, the inoculum composition is diluted with water before inoculation.

A further embodiment includes, an inoculum composition comprising: a diluent and an isolated toxigenic endophyte, for example an isolated toxigenic endophyte selected from a strain having all of the identifying characteristics of a strain deposited under Accession number CBS 127938, CBS 127939, CBS 127940, CBS 127941, and/or CBS 127942, grown in a culture medium under conditions wherein the endophyte cells are in clusters of mycelia or spores and wherein the clusters are less than 5 mm in diameter or length, optionally less than 10 mm in diameter or length, and comprise the following characteristics: i) capable of colonizing white pine seedling, and ii) producing in planta a compound toxic to a fungal pest such as a rust in a disc diffusion assay.

Toxigenic endophytes produce toxin compounds that are toxic to fungal pests such as rust. Toxin compounds of several toxigenic endophyte strains have been identified and are described in Table 1. A particular toxigenic endophyte may produce more than one toxin compound. Combinations of toxigenic endophytes can also for example provide a broader spectrum of compounds. As the toxigenic endophytes produce compounds that are toxic to fungal pests, isolated toxigenic endophytes can be used to prepare white pine seedlings colonized with the toxigenic endophytes.

(IV) Methods And Uses

Antifungal Uses

It is demonstrated herein that compounds of the formula (I), (II), (III), (IV), (V) and/or (VI) isolated from toxigenic endophytes are antifungal in disc diffusion assays. For example, each of the compounds possessed antifungal properties when tested with yeast in disc diffusion assays. Compounds 1, 2 and 5 were also tested with rust *Microbotryum violaceum* and also found to be antifungal.

Accordingly, an aspect of the disclosure is use of an effective amount of an antifungal composition comprising a compound of the formula (I), (II), (III), (IV), (V), and/or (VI) and/or combinations thereof as an antifungal.

Another aspect of the disclosure includes a method of inhibiting fungal growth on a fungal prone structure comprising contacting the fungal prone structure, with an amount of a composition comprising an anti-fungal effective concentration of a compound of the formula (I), (II), (III), (IV), (V), and/or (VI) and/or combinations thereof.

Another aspect is use of an effective amount of an antifungal composition comprising a compound of the formula (I), (II), (III), (IV), (V), and/or (VI) for treating a tree infected with a fungus. An embodiment, is use of an effective amount of an antifungal composition comprising a compound of the formula (I), (II), (III), (IV), (V), and/or (VI) for treating a tree to prevent infection with a fungus.

Another aspect includes a method for the treatment or prevention of fungal infection, comprising: topically applying to an area of a tree in need thereof, an effective amount of a composition comprising an effective amount of a compound of the formula (I), (II), (III), (IV), (V), and/or (VI).

In an embodiment, the composition is applied by spraying. In an embodiment, the composition is applied to a surface of the tree, such as the needles.

Given the broad spectrum of activity (e.g. yeasts and rusts), it is expected that the compounds will be antifungal to a variety of fungi, when for example topically applied.

Another aspect of the disclosure includes a method of inhibiting fungal growth comprising contacting a fungal prone structure, with an amount of a composition comprising an anti-fungal effective concentration of a compound of the formula (I), (II), (III), (IV), (V), and/or (VI) and/or combinations thereof.

(V) Methods Of Inoculating White Pine Seeds And Seedlings

The inventors have previously devised methods to propagate toxigenic endophytes and have demonstrated that conifer seedlings can be inoculated with toxin-producing endophyte strains during a susceptible time window. Inoculation during the susceptible time period permits colonization of the conifer by the toxigenic endophyte non-invasively. The inventors have also previously shown that toxigenic endophyte colonization persists and spreads to non-inoculated new growth branches as well as to neighbouring seedlings. Further these methods are, as shown by the inventors, amenable to large-scale production in a commercial setting.

Methods for inoculating conifer seedlings, for detecting successfully inoculated plants, for preparing an effective inoculum composition, as well as methods of producing toxigenic endophyte colonized conifer plants that are resistant to pests were described in U.S. application Ser. No. 12/447,217 filed: Oct. 24, 2007 titled, ENDOPHYTE ENHANCED SEEDLINGS WITH INCREASED PEST TOLERANCE, which is hereby incorporated by reference.

The inventors have now isolated several new endophyte strains from *Pinus strobus* and have identified the major toxin profile these endophyte strains. Isolation from white pine is indicative that white pine are receptive to colonization by the isolated toxigenic endophytes, using for example a method described herein.

Accordingly, an aspect of the disclosure provides a method of colonizing a white pine seedling with a toxigenic endophyte comprising inoculating a white pine seedling or a white pine seed with a composition and/or carrier comprising a toxigenic endophyte during a susceptible time window when the white pine seedling or white pine seed is susceptible to colonization by the toxigenic endophyte, under conditions wherein the toxigenic endophyte colonizes the seedling and produces a compound selected from a compound of the formula (I), (II), (III), (IV), (V) and/or (VI) and/or combinations thereof.

In an embodiment, the method is for colonizing one or more white pine seedlings.

In an embodiment, the method further comprises growing the seedling or germinating and growing the conifer seed.

Another aspect of the disclosure provides a method of colonizing a population of white pine seedlings with one or more toxigenic endophytes comprising inoculating one or more white pine seedlings or one or more white pine seeds with a composition and/or carrier comprising one or more toxigenic endophytes during a susceptible time window when the white pine seedlings or white pine seeds are susceptible to colonization by the toxigenic endophyte, under conditions wherein at least one of the toxigenic endophytes colonizes one or more seedlings and produces a compound selected from a compound of the formula (I), (II), (III), (IV), N) and/or (VI) and/or combinations thereof.

In another aspect, the disclosure includes a method of making a colonized white pine seed comprising inoculating a white pine seed with a composition comprising a toxigenic endophyte during a susceptible time window when the white pine seed is susceptible to colonization by the toxigenic endophyte under conditions wherein the toxigenic endophyte colonize the seedling and produces a compound selected from a compound of the formula (I), (II), (III), (IV), (V) and/or (VI).

In another aspect, the disclosure includes a method of making a population of colonized white pine seeds comprising inoculating white pine seeds with a composition comprising one or more toxigenic endophytes during a susceptible time window when the white pine seeds are susceptible to colonization by the toxigenic endophytes under conditions wherein at least one of the toxigenic endophytes colonizes the one or more seedlings and produces a compound selected from a compound of the formula (I), (II), (III), (IV), (V) and/or (VI).

In another aspect the disclosure further includes, culturing the white pine seedling or seedlings, under conditions wherein the or at least one of the toxigenic endophytes colonizes the seedling or seedlings and produces a compound selected from a compound of the formula (I), (II), (III), (IV), (V) and/or (VI).

In an embodiment, the endophyte produces a compound of the formula (IV), (V) and/or (VI).

In an embodiment, the method further comprises growing the seedling or germinating and growing the conifer seed to obtain the colonized white pine seed or colonized white pine seedling.

In an embodiment, the method is for producing a seedling that has increased resistance to a pest such as a fungal pest.

In another embodiment, the disclosure includes a method of preparing a white pine seedling with increased tolerance to a pest, comprising inoculating a white pine seedling or a white pine seed with a composition and/or carrier comprising a toxigenic endophyte during a susceptible time window when the white pine seedling or seed is susceptible to colonization by the toxigenic endophyte and culturing the white pine seedling or white pine seed, under conditions wherein the toxigenic endophyte colonizes the seedling, and produces a compound selected from a compound of formula (I), (II), (III), (IV), (V) and/or (VI) and/or combinations thereof.

In an embodiment, the method is for preparing a population of white pine seedlings or white pine seeds with increased tolerance to a pest.

In an embodiment, the susceptible time window for a white pine seedling comprises and/or consists of the period post germination during sustained elongation of the seedling shoot apex when the number of intermediately developed and juvenile needles is greater than the number of needles that are completely developed and mature and the cuticle is fully formed and the susceptible time window for a white pine seed is during seed stratification.

In an embodiment, more than one white pine seedlings are inoculated and the composition comprises more than one toxigenic endophyte. The more than one toxigenic endophytes are optionally inoculated at the same time or sequentially. In an embodiment, a crop of seedlings is inoculated.

In an embodiment, the method further comprises culturing the white pine seedling or white pine seed after inoculating. The culturing can for example in a same or different location as the inoculation. For example the inoculation can be in a nursery (e.g. greenhouse or outdoor rearing facility) and the culturing can be for example in a nursery.

In an embodiment, the white pine seed and/or the white pine seedling is cultured for a time and under conditions to permit and/or promote colonization by the toxigenic endophyte. For example, high humidity for example greater than 80% can promote colonization. Seedlings are optionally sprayed late in the day so composition comprising toxigenic endophyte stays on foliage longer.

In an embodiment, the method further comprises growing the seedling or germinating and growing the conifer seed to obtain the colonized white pine seed or colonized white pine seedling.

The internal transcribed spacer (ITS) regions of ribosomal DNA (rDNA) of the isolated strains have been sequenced and sequence analysis reveals that the deposited strains are likely all *Lophodermium* species.

In an embodiment, the toxigenic endophyte is an endophyte of the *Lophodermium* species which produces a compound selected from a compound of formulae (I), (II), (III), (IV), (V) and/or (VI) and/or combinations thereof.

In an embodiment, the compound produced by the toxigenic endophyte is selected from a compound of the formula (IV), (V) and/or (VI). In an embodiment, the compound is selected from pyrenophorol, dihydropyrenophorin and/or pyrenophorin and/or combinations thereof.

In another embodiment, the endophyte is a strain having all of the identifying characteristics of a strain deposited under the Accession number CBS 127939, which was deposited Sep. 29, 2010, Centraalbureau voor Schimmelcutures, Uppsalalaan 8, P.O. Box 851673508 AD Utrecht, The Netherlands; an endophyte comprising SEQ ID NO:3, and/or an endophyte comprising an Internal Transcribed Spacer (ITS) region having at least 99% sequence identity to SEQ ID NO:3.

In an embodiment, the toxigenic endophyte produces one or more compounds selected from a compound of the formula (I), (II) and/or (III).

In an embodiment, the toxigenic endophyte is selected from the group:
a) a strain producing a compound selected from a compound of the formula (I), (II), (III), (IV), (V) and/or (VI),
b) a strain having all of the identifying characteristics of a strain deposited under the Accession number CBS 127938, CBS 127940, CBS 127941, and/or CBS 127942, deposited Sep. 29, 2010, Centraalbureau voor Schimmelcutures, Uppsalalaan 8, P.O. Box 851673508 AD Utrecht, The Netherlands; b) an endophyte comprising any one of SEQ ID NO: 4 to 7; and/or an c) endophyte comprising an Internal Transcribed Spacer (ITS) region having at least 99% sequence identity to any one of the sequences in b).

In another embodiment, the composition comprises toxigenic endophyte hyphal fragments, optionally at least 1-25 toxigenic endophyte hyphal fragments/6 microliter, optionally at least 1-4 toxigenic endophyte hyphal fragments/microliter, optionally at least 0.2-4 toxigenic endophyte hyphal fragments/microliter.

In a further embodiment, the composition comprises at least 3 toxigenic endophyte hyphal fragments per 6 microliter.

Various methods can be used to inoculate a white pine seedling. In another embodiment the inoculation method comprises contacting an inoculum composition with a surface of a conifer seedling. In another embodiment, the inoculation method comprises contacting carriers comprising inoculum composition such as pine needles soaked in inoculum composition with a seedling growth medium. Accordingly, in an embodiment, the inoculating comprises contacting the white pine seedling with the toxigenic endophyte by i) contacting a surface of the white pine seedling with the toxigenic endophyte or ii) contacting a seedling growth medium supporting the white pine seedling with the carrier comprising the one or more toxigenic endophytes.

Inoculation under humid conditions, for example, greater than 70%, or 80% can promote seedling colonization. Seedlings are optionally contacted with inoculum e.g. sprayed late in the day so the inoculum composition comprising toxigenic endophyte stays on foliage longer In an embodiment, the inoculation comprises contacting a seedling or seed with inoculum, and incubating or culturing the seedling or seed under conditions that permit the inoculum to remain in contact with the seedling or seed for at least 1 hour, 2 hours, 3 hours, 4 hours, 5 hours, 6 hours, 7 hours, 8 hours, 9 hours, 10 hours or at least 12 hours. In another embodiment, the inoculation comprises contacting the seedling with inoculum and incubating or culturing the seedling under conditions that permit liquid droplets of the inoculum to persist for at least 1 hour, 2 hours, 3 hours, 4 hours, 5 hours, 6 hours, 7 hours, 8 hours, 9 hours, 10 hours or at least 12 hours on the seedling. In an embodiment, the method comprises inoculating seeds, the inoculation comprising contacting a seed with inoculum (e.g soaking) and incubating or culturing the seed for at least 1 hour, 2 hours, 3 hours, 4 hours, 5 hours, 6 hours, 7 hours, 8 hours, 9 hours, 10 hours or at least 12 hours.

An inoculum composition is optionally applied to a conifer seedling by spraying a surface area of a conifer seedling with the inoculum composition. Accordingly in an embodiment, the inoculating comprises spraying the seedling with the composition comprising the one or more toxigenic endophytes.

In another embodiment, the spraying comprises a spraying method selected from the group of misting, ground spraying, bottle spraying, boom spraying.

In a further embodiment, the spraying method comprises boom spraying or bottle spraying. In an embodiment the inoculum composition is applied or delivered using a boom sprayer and an injector pump to inject the inoculum composition into an irrigation line. Inoculation is readily applied for example during a time when the seedling would remain moist for the longest period of time and optionally comprises repeated application on the same or different days. In an embodiment, boom spraying comprises, providing a boom sprayer, an irrigation line connected to the boom sprayer, and an injector pump, the injector pump injecting the composition into the irrigation line and the boom sprayer spraying the composition onto the white pine seedling.

The methods of inoculation described above can be combined as well as repeated. In an embodiment the methods of inoculation that are combined and/or repeated comprise the same method of inoculation. In another embodiment, the methods combined and/or repeated are different methods of inoculation. For example in an embodiment, a white pine seedling is first inoculated during seed stratification and then inoculated during the period of sustained elongation of the shoot apex.

In other embodiments, the inoculum composition optionally comprises additives that improve and/or increase uptake of a toxigenic endophyte. A number of chemicals and or preparations are known in the art that would facilitate inoculum uptake. For example additives may reduce the drying time after spraying. In an embodiment the additive is a carbohydrate. In another embodiment the carbohydrate is selected from the group comprising sugars. In another embodiment the carbohydrate is a carbohydrate like CMC. Further fluorescent tracers may be added to the inoculum composition to determine the amount of spray deposited.

Delivery of an inoculum composition may be performed by combining or repeating methods including spraying. Optionally the inoculum composition may be delivered by repeated spraying.

In an embodiment, trees planted in the vicinity of infected trees (e.g. where cast would fall) are inoculated, by horizontal transmission. Accordingly, in an embodiment, the invention provides a method of inoculating or transmitting an endophyte to a white pine seedling by horizontal transmission comprising placing a seedling in the vicinity of a colonized white pine seedling. In an embodiment, the vicinity comprises an area or zone where cast needles would fall. In an embodiment the area comprises a 0.25 metre radius around the colonized conifer. A person skilled in the art will recognize that the area where cast needles would fall depends on such factors as colonized tree size. In another embodiment, the method further comprises detecting the transmitted endophyte in the seedling. A suitable radius range in an embodiment is up to 250 cm.

In another embodiment, the white pine seedlings are inoculated by placing a carrier comprising toxigenic endophytes in contact with the seedling growing medium (for example on the soil surface). In an embodiment, the inoculating comprises contacting the seedling growth medium with the carrier, wherein the carrier comprises a conifer needle comprising the toxigenic endophytes, optionally comprising the toxigenic endophyte on the conifer needle surface or within the conifer needle. In an embodiment the carrier comprises irradiated conifer needles. In another embodiment, the seedling is planted in a growing medium, and irradiated conifer needles colonized by toxigenic endophytes or other conifer plant parts colonized by toxigenic endophytes are added to the growing medium. In another embodiment the growing medium, comprises potting mix surrounding or supporting the conifer seedling to be inoculated. In another embodiment the growing medium or potting mix comprises soil. The needles comprising toxigenic endophyte may be directly contacted or indirectly contacted with the conifer seedling. For examples, needles may be placed in direct physical contact with the seedling or may be placed in indirect contact with the seedling by contacting needles with the potting mix supporting seedling growth.

In an embodiment, the quantity of toxigenic endophyte inoculated is approximately 10 propagules/microliter.

In another embodiment, the white inoculating step comprises contacting the white pine seed with the composition during seed stratification.

In an embodiment, the white pine seed or seeds is/are contacted with the composition comprising the toxigenic endophyte by soaking the seed or seeds in the composition, optionally wherein the seed is soaked for at least least 1 hour, 2 hours, 3 hours, 4 hours, 5 hours, 6 hours, 7 hours, 8 hours, 9 hours, 10 hours or at least 12 hours, optionally overnight, drained and optionally refrigerated at 2-6° C.

In another embodiment, the inoculating is repeated.

In a further embodiment, the inoculating is selected from spraying the seedling and soaking the seed with the composition.

In another embodiment, the method comprises inoculating the white pine seed during seed stratification and inoculating a seedling germinated from the white pine seed during the susceptible time window.

In another embodiment, the method further comprises determining whether the endophyte has colonized the white pine seedling by contacting a sample of the white pine seedling with a detection agent specific for a component of the toxigenic endophyte and/or a compound produced by the toxigenic endophyte, a derivative, metabolite or plant derived form, wherein detection of the component and/or compound is indicative of colonization. In an embodiment, the detection agent is an antibody.

A component of the toxigenic endophyte can be detected using an antibody specific for example for pest protein, wherein the antibody preferentially binds the pest protein compared to other proteins. The assay is optionally an ELISA assay, a hand-held immunoblot based assay and/or an antibody assay contained in a kit. Also, a compound produced by the toxigenic endophyte, a derivative, metabolite or plant derived form can be detected using for example NMR, thin layer chromatography, HPLC, HPLC-Mass Spectroscopy based methods, column chromatography as well as other analytical methods.

For example, compounds of the formula (I), (II), (III), (IV), (V) and/or (VI) have been detected in toxigenic endophytes isolated from white pine as described herein. The major metabolites, their derivatives, or degradation products may be used as a proxy for toxicity, and/or detection of colonization.

The presence of a toxigenic endophyte may not be detectable in a successfully colonized seedling until the seedling has grown for a period of time. In an embodiment, the detecting step is performed on a sample obtained from an inoculated white pine, after the white pine has grown at least 2 months, at least 3 months, at least 4 months, at least 5 months, at least 6 months, at least 7 months, at least 8 months, at least 9 months, at least 10 months, at least 11 months, or at least 12 months post inoculation. In an embodiment, the sample is obtained when the plant is within 12 to 18 months post inoculation. In an embodiment, where the method comprises more than one inoculation, the period of growth is post a first inoculation. In another embodiment, the period of growth is post a second inoculation. In an embodiment, the sample comprises a needle proximal to the site of inoculation.

Toxigenic endophytes can spread to other branches and spread to other seedlings within the vicinity of the colonized tree. A person skilled in the art will recognize that the sample can be obtained many months past inoculation and can be obtained from a tissue proximal or distal to the inoculation site. For example, a person skilled in the art would recognize that branches adjacent to the site of inoculation are likely to be positive at earlier time points than branches further from the site of inoculation. Similarly, several branches can be tested when assaying a conifer for colonization. Detection of toxigenic endophyte or toxin compound for example in 2, 3, 4, 5, 6, 7, 8 or 9 samples is sufficient to indicate the white pine is colonized.

In another embodiment, the compound in the white pine seedling is in sufficient concentration to reduce pest infection rate (e.g. the number of needles or seedlings infected) compared to a non-inoculated white pine seedling or seedlings.

In another embodiment, the pest infection rate is inhibited by at least 5%, optionally 10% relative to a control.

In yet another embodiment, the pest infection rate is inhibited by 10-30% relative to a control.

In a further embodiment, the pest infection rate is assessed using an in vivo pest toxicity assay.

In an embodiment, the compound is present in a white pine needle of a colonized seedling in an amount of at least 0.15 microgram per gram of needle.

In another embodiment, the compound is present in a white pine needle from a colonized seedling in an amount of at least 5 micromolar, 10 micromolar, 25 micromolar, 50 micromolar and 100 micromolar.

As described above, the susceptible time window comprises an optimal time for inoculating a white pine seedling. As mentioned the susceptible time window of a seedling includes the period post generation during sustained elongation of the seedling shoot apex when the number of intermediately differentiated needles is greater than the number of needles that are completely differentiated. This can be correlated to shoot length, seedling height and/or weeks post germination.

In an embodiment, the white pine is inoculated when the shoot length is greater than 10 mm and less than 100 mm.

In an embodiment, the white pine seedling is inoculated when the seedling is at least 1 cm high and less than 10 cm high, when the seedling is at least 1 cm high and less than 6 cm high, when the seedling is at least 2 cm high and less than 4 cm high, and/or when the seedling is at least 3 cm high. In another embodiment the seedling is inoculated when about 1-2 cm tall, about 2-3 cm tall, about 3-4 cm tall, about 4-5 cm tall, about 5-6 cm tall, about 6-7 cm tall, about 7-8 cm tall, about 8-9 cm tall, about 9-10 cm tall. In an embodiment, the seedling is inoculated at about 3 cm tall (e.g. 2-4 cm tall).

In another embodiment, the white pine seedling is inoculated between about 2 weeks to about 16 weeks post germination, about 6 weeks to about 10 weeks post germination, about 7 weeks to about 9 weeks post germination and/or when the white pine seedling is about 8 weeks post-germination. In another embodiment seedling is inoculated at about 2-3 weeks, about 3-4 weeks, about 4-5 weeks, about 5-6 weeks, about 6-7 weeks, about 7-8 weeks, about 8-9 weeks, about 9-10 weeks post-germination.

In an embodiment, the pest is a fungus associated with disease, optionally a rust fungus, optionally *Cronartium ribicola*.

In an embodiment, the pest causes white pine blister rust.

In an embodiment, the inoculating is preceded by isolating a toxigenic endophyte from a donating plant and culturing the toxigenic endophyte, wherein the toxigenic endophyte produces a compound selected from a compound of the formula (I), (II), (III), (IV), (V) and/or (VI), optionally comprising the additional step of harvesting the isolated toxigenic endophyte; and resuspending the harvested endophyte in a diluent.

In another embodiment, the disclosure includes use of a toxigenic endophyte to prepare a white pine seedling with increased tolerance to a pest comprising inoculating the white pine seedling or a white pine seed with a composition comprising a toxigenic endophyte and culturing the white pine seedling or seed under conditions suitable for colonization of the white pine seedling by the toxigenic endophyte.

In an embodiment, white pine seedlings inoculated according to a method or use described herein are grown for a time and under conditions suitable to permit and/or promote colonization and further cultured, e.g. grown, for example to obtain a white pine plant of a particular age or size and/or to obtain a white pine tree.

In an embodiment, the colonized white pine seed is grown for a time and under conditions suitable to obtain a white pine seedling or white pine plant.

In an embodiment, the white pine seedling is grown for at least 2 months, 3 months, 4 months, 6 months, 8 months, 12 months, 15 months, 18 months, 21 months or 24 months or any number of months in between 8 and 24 months.

Accordingly, a further aspect comprises a white pine plant or part thereof colonized by an isolated toxigenic endophyte that produces a compound that retards pest infection rate, wherein the white pine plant was grown from a seedling colonized according to a method described herein.

In an embodiment, the white pine is a tree, seedling, shrub, or hedge.

In an embodiment, the part thereof is a needle. Needles that harbour toxigenic endophytes can be used for example to colonize nursery plants by for example contacting a white pine seedling growth medium with the needle. In an embodiment, the part thereof is a tissue or isolated conifer cell culture.

In an embodiment, the white pine is colonized by a toxigenic endophyte comprising a sequence selected from the group consisting of SEQ ID NOS: 3-7, preferably selected from strains having all of the identifying characteristics of strains deposited under Accession numbers CBS 127938, CBS 127939, CBS 127940, CBS 127941 and/or CBS 127942.

A further aspect includes a method of isolating a candidate toxigenic endophyte comprising contacting an endophyte nucleic acid, optionally DNA, with a probe, the probe comprising a sequence corresponding to at least 50 nucleotides of sequence selected from the group consisting of SEQ ID NOS: 3-7, wherein an endophyte with at least: 90%, 91%, 92%, 93%, 94%, 95%, 96%, 97%, 98% or 99% sequence identity is a candidate toxigenic endophyte.

Toxicity to a pest can be assessed using a pest toxicity assay including in vivo and in vitro assays. For example, standard assays including yeast assays and disc diffusion, agar and broth dilution techniques such as the Oxford assay (Vincent and Vincent, 1944) can be employed. The toxicity of an endophyte toxin compound or candidate endophyte toxin compound can be assessed by incorporating the compound into an artificial diet suitable for pest growth. The artificial diet can be prepared in individual plates, for example containing toxin compound concentrations of 5 micromolar, 10 micromolar, 25 micromolar, 50 micromolar and 100 micromolar. An example of an in vivo pest toxicity test includes contacting needles and/or branches of white pine seedlings treated with a composition comprising a compound of and/or colonized with a toxigenic endophyte with different concentrations of a fungal pest for different durations of exposure and measuring for example fungal growth rate and/or extent of fungal infection or fungal colonization.

The appropriate time period for leaving a pest in contact with the needles and/or branches, will vary with factors such the type of pest, and if out doors, weather conditions. In an embodiment, the time period is optionally between 1-14 days, for example, 3-7 days. One skilled in the art would understand that various methods can be modified to test different concentrations of toxin compounds and that the conditions can be modified to test a variety of different pests.

Also provided in a further aspect is an isolated nucleic acid sequence comprising:
  a) a nucleic acid sequence selected from the group consisting of SEQ ID NO:3-7;
  b) a nucleic acid sequence that is complimentary to a nucleic acid sequence of (a);
  c) a nucleic acid sequence that has substantial sequence homology to a nucleic acid sequence of (a) or (b);
  d) a nucleic acid sequence that is an analog of a nucleic acid sequence of (a), (b) or (c); or
  e) a nucleic acid sequence that hybridizes to a nucleic acid sequence of (a), (b), (c) or (d) under stringent hybridization conditions.

The following non-limiting examples are illustrative of the present disclosure:

EXAMPLES

Example 1

Highlights

The extracts of five foliar fungal endophytes from *Pinus strobus* (eastern white pine) showed antifungal activity in disc diffusion assays.

A new aliphatic polyketide and three new related sesquiterpenes were isolated and characterized.

Additionally, the three known macrolides; pyrenophorol, dihydropyrenophorin and pyrenophorin were isolated and identified.

Structures were elucidated by 2D NMR and LC-HRMS.

The isolated compounds were tested for antifungal activity against *Saccharomyces cerevisae* and the rust *Microbotryum violaceum*.

Endophytes from the needles of superior *Pinus strobus* (eastern white pine) trees originating in New Brunswick, Nova Scotia, Quebec and Prince Edward Island, Canada were isolated. Fungi were collected form surface disenfeted needles using the metod of Johnson and Whitney (1989) and stored on 2% malt extract agar slants (Difco). Strains were cultured using established procedures and the extract from each endophyte was tested for antifungal activity to *Saccharomyces cerevisae*. Strains that exhibited toxicity were analysed by LC-HRMS and the major metabolites were isolated by LC-MS-SPE. Here is reported the characterization by NMR and MS of the major metabolites from five of these endophytes.

The extracts of five foliar fungal endophytes isolated from *Pinus strobus* (eastern white pine) that showed antifungal activity in disc diffusion assays (e.g. Oxford assay, Vincent and Vincent 1944) were selected for further study. From these strains the new aliphatic polyketide compound 1 and three related sesquiterpenes (IIa), (IIb) and (III) were isolated and characterized (see FIG. 1). Compound (III) is reported for the first time as a natural product and the E/Z conformational isomers (IIa) and (IIb) are reported as new structures (see FIG. 1). Additionally, the three known macrolides; pyrenophorol (IV), dihydropyrenophorin (V) and pyrenophorin (VI) were isolated and identified. Their structures were elucidated by spectroscopic analyses including 2D NMR, HRMS and by comparison to literature data where available. All 5 isolated compounds were tested for antifungal activity against *Saccharomyces cerevisae* and the isolated compounds 1, (III) and (IV) were tested for antifungal activity against both the rust *Microbotryum violaceum* and *Saccharomyces cerevisae*.

Results 2.1. Screening

Five strains were selected from the original 35 isolated from superior *P. strobus* trees. These were selected based on the antifungal activity of crude extracts and preliminary LC-HRMS analysis. The results of the DNA sequencing for all five strains show that they are all species of *Lophodermium* (Deckert et al, 2002).

2.2. Toxicity

Initial antifungal testing showed that the extracts from all five endophytes were antifungal to *S. cerevisae*. The results of the Oxford disc assay using the isolated compounds confirmed these observations for both *S. cerevisae* and *Microbotryum violaceum*. A quantitative test protocol based on cell density using OD measurements at 600 nm in 96 well microplates was employed. Statistically-significant reductions in cell density were seen for compounds 1, (III) and (IV) at 24 hours against *S. cerevisae* (ANOVA, p<0.000) and at 48 hours against *M. violaceum* (ANOVA, p<0.000) as compared to controls, with compound (III) being the most antifungal based on results of the response at 24 h.

2.3. Isolation and Structure Determination

Following the initial screening, the extracts were analyzed using LC-MS-SPE/NMR, where a number of the major metabolites were isolated on GP resin cartridges. The compounds were then transferred directly using 160 μL of deuterated solvent into 3 mm NMR tubes for acquisition of 1D and 2D NMR data. Structures were elucidated primarily by analysis of HRMS and NMR data, as well as comparison with literature data where available. The five strains studied produced an aliphatic polyketide metabolite 1, three related sesquiterpenes (IIa), (IIb) and (III) and three known macrolides (IV), (V) and (VI) (see Table 1).

(i) (2Z,4E)-methyl-6-acetoxy-5-formyl-7-oxo-octa-2,4-dienoate

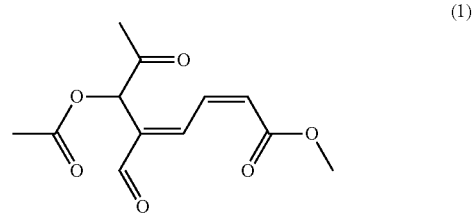

(2Z,4E)-methyl 6-acetoxy-5-formyl-7-oxoocta-2,4-dienoate

Compound 1 was assigned the formula $C_{12}H_{14}O_6$ based on HRMS analysis. It was isolated as the major metabolite from CBS 127938 and CBS 127942. All 14 protons were identified in the $^1$H NMR spectrum (see Table 2), with one in the very downfield region at δ 9.57 (s), three protons in the unsaturated region δ 8.39 (dd, J=11.8/0.8), δ 7.23 (dd, J=11.4/11.8) and δ 6.22 (dd, J=11.4/0.8) that through coupling analysis were shown to originate from two conjugated double bonds, two protons from an oxygen-bound $CH_2$-group δ 6.15 (s), a methoxy group at δ 3.76 (s), as well as two other methyl groups, at δ 2.11 and δ 2.08, appearing as singlets. Analysis of HSQC and HMBC data identified the presence of several carbonyl moieties; an aldehyde, a ketone and two esters. On the basis of the HMBC data, especially the correlations from H-6 to C-4, C-5, C-7, C-8 and C-10, as well as correlations from H-7 and H-9 the structure for compound 1 was determined.

(ii) Compounds (IIa)

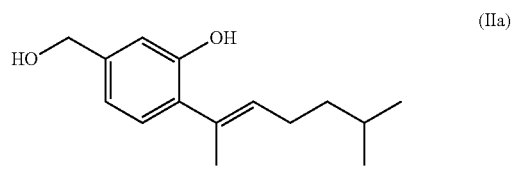 [SMILES: C/C(=C\CCC(C)C)c1ccc(CO)cc1O]

Compound (IIa) was isolated from CBS 127938, CBS 127940, CBS 127941 and CBS 127942, and was assigned the molecular formula $C_{15}H_{22}O_2$, which differs from the formula of compound (IIa) only by one oxygen atom. The $^1$H NMR spectrum showed that the loss of an oxygen had occurred with a ring-opening, and reduction of the bond between C-2' and C-3'. This was evident, as there were still signals from three methyl groups, but the $CH_2$ group was lost, and an unsaturated proton signal appeared (δ 5.43, tq, J=7.2/0.7 Hz). HSQC and HMBC data confirmed this assumption, as both signals from carbon atoms in the ether bond were no longer present, and correlations throughout the molecule proved no changes in the other parts of the molecules. The double-bond was assigned as the E-configuration based on the lack of a NOE correlation between H-3' and H-9' as was observed for the Z-isomer (IIb).

(iii) Compound (IIb)

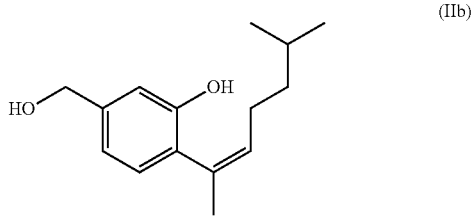 [SMILES: C/C(=C/CCC(C)C)c1ccc(CO)cc1O]

(IIb)

Compound (IIb) was only isolated from CBS 127940, but analysis of LC-HRMS data of the crude extracts showed that it was also present in CBS 127941 and CBS 127942. The molecular formula of (IIb) was found to be identical to (IIa). The 1D and 2D NMR data were also similar with only small changes in δ values, the difference between the two compounds was at the configuration of the double bond. This was supported by the finding that H-9' and H-3' had NOE correlations, assigning compound (IIb) Z-configuration.

(iii) Compound of the Formula (III)

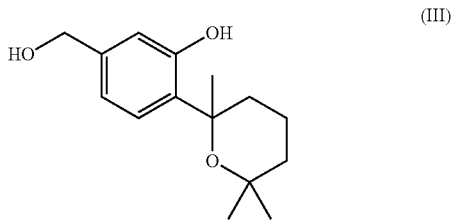 [SMILES: CC1(C)CCCC(C)(c2ccc(CO)cc2O)O1]

(III)

Compound (III) was assigned the formula $C_{15}H_{22}O_3$ on the basis of HRMS, and was isolated from CBS 127938, CBS 127940 and CBS 127942. The $^1$H NMR data (see Table 3) shows signals for three aromatic protons at δ 7.07 (d, J=7.9 Hz), δ 6.78 (dd, J=7.9 and 1.6 Hz) and δ 6.73 (d, J=7.9 Hz), suggesting the presence of a 1,2,5-trisubstituted aromatic ring in the molecule. Additionally, three singlet methyl groups at δ 1.43, 1.23 and 0.93; four methylene groups, three as multiplets, and giving rise to several signals due to diastereotopic nature of the protons (δ 2.43, 1.73, 1.68, 1.62 and 1.52), and one as a doublet (δ 4.48, J=5.9 Hz) were observed. Furthermore, two single protons were observed, at δ 9.06 (s) and 3.01 (t, J=5.9 Hz). HSQC and HMBC spectra contained signals for 15 carbon atoms, of which five were quarternary. Three of these were substituted aromatic carbons (δ 157.5, 142.8 and 130.8), with the down-field signal originating from an oxygen-bearing carbon. Two other quarternary carbons at δ 78.5 and 75.3 respectively, were also identified as oxygen-bearing carbon atoms. Furthermore, signals from three aromatic CH carbons were present (δ 126.1, 118.8 and 116.5), as well as four $CH_2$ carbons (δ 64.5, 37.8, 34.8 and 17.6), with the signal at δ 64.5 confirming the presence of a $CH_2$—OH group. Three additional signals (δ 32.6, 32.0 and 25.7) corresponded to the three methyl groups detected in the $^1$H NMR spectrum. The HSQC spectrum revealed that the protons at δ 3.01 and 9.06 were not directly attached to a carbon atom, which led to the assignment of these as an aliphatic alcohol, and a phenol respectively. The position of substituents on the aromatic ring was assigned based on HMBC correlations, as H-7 has correlations to C-4, C-5 and C-6, attaching this substituent to C-5. The chemical shift value of C-3 places the phenol at this position, as well as the HMBC correlations to C-2' from H-3, and to C-2 from H-9'. The presence of diastereotopic protons was revealed by HSQC data, and the skeleton of the heterocyclic ring was determined based on COSY and HMBC correlations. The position of the methyl groups was revealed through HMBC correlations from H-7' and H-8' to C-5', C-6' and between methyl groups. H-9' showed HMBC correlations to C-2, C-2' and C-3', attaching this group to C-2'. Compound (III) is a new natural product, but has previously been reported as an intermediate in a synthesis of sydowic acid (Serra, 2000). The reported OR of $[\alpha]^{20}_D$=+40 (c 2.2, $CHCl_3^-$) did not agree with our data that showed zero rotation. Further chiral LC-HRMS analysis identified two peaks with the correct mass separated by 1.3 min, revealing that compound (III) was in fact a ~60:40 mixture of enantiomers.

(iv) Compounds (IV), (V) and (VI)

Pyrenophorol (IV): $[\alpha]^{25}_D$=−7.4 (c 1, $CHCl_3$); $^1$H NMR ($CD_3CN$, 600 MHz) δ 6.78 (2H, dd, $J_{H-3,H-2}$=15.76, $J_{H-3,H-4}$=6.66, H-3), 5.82 (2H, dd, $J_{H-2,H-3}$=15.76, $J_{H-2,H-4}$=1.16, H-2), 4.99 (2H, m, H-7), 4.06 (2H, m, H-4), 3.21 (2H, d, $J_{OH,H4}$=4.37, OH) 1.76 (2H, m, H-5A), 1.68 (2H, m, H-6A), 1.64 (2H, m, H-5B), 1.51 (2H, m, H-6B), 1.21 (6H, d, $J_{CH3,H-7}$=6.56, $CH_3$); $^{13}$C NMR ($CD_3CN$, 150 MHz, from HSQC and HMBC correlations) δ 166.7 (2×C, C-1), 150.4 (2×CH, C-3), 122.4 (2×CH, C-2), 71.0 (2×CH, C-4), 70.5 (2×CH, C-7), 31.4 (2×$CH_2$, -5), 29.4 (2×$CH_2$, C-6), 18.5 (2×$CH_3$, $CH_3$); HRMS m/z 313.1648 $[M+H]^+$ (calc. for $[C_{16}H_{25}O_6]^+$, 313.1646).

Dihydropyrenophorin (V): $^1$H NMR ($CD_3CN$, 600 MHz) δ 6.93 (1H, dd, $J_{H3',H2'}$=15.72, $J_{H3',H\ 4'}$=4.49, H-3'), 6.87 (1H, d, $J_{H-3,H-2}$=16.15, H-3), 6.52 (1H, d, $J_{H2,H3}$=16.15, H-2), 5.89 (1H, d, $J_{H2',H3'}$=15.72, $J_{H-1',H-4'}$=1.66, H-2'), 5.05 (1H, m, H-7'), 4.91 (1H, m, H-7), 2.71 (1H, ddd, $J_{H-5A,H-5B}$=13.7, $J_{H-5A,H6}$=9.3, $J_{H5A,H6}$=4.11, H-5A), 2.60 (1H, m, H-5B), 2.01 (2H, m, H-6), 1.85 (1H, m, H-6A), 1.76 (1H, m, H-6B, 1.73 (1H, m, H-5'A), 1.60 (1H, m, H-5'B), 1.23 (3H, d, $J_{H-7'-CH3,\ H-7'}$=6.51, 7'-$CH_3$), 1.20 (3H, d, $J_{7-CH3,\ H-7}$=6.27, 7-$CH_3$); $^{13}$C NMR ($CD_3CN$, 150 MHz, from HSQC and HMBC correlations) δ 203.0 (C, C-4), 167.3 (C, C-1'), 166.1 (C, C-1), 150.4 (CH, C-3'), 140.7 (CH, C-3), 131.9 (CH, C-2), 71.9 (CH, C-7'), 71.0 (CH, C-7), 69.7 (CH, C-4'), 36.2 ($CH_2$, C-5), 32.6 ($CH_2$, C-6), 31.4 ($CH_2$, C-5'), 28.5 ($CH_2$, C-6'), 19.8 ($CH_3$, 7-$CH_3$), 18.1 ($CH_3$, 7'-$CH_3$); HRMS m/z 311.1481 $[M+H]^+$ (calc. for $[C_{16}H_{23}O_6]^+$, 311.1489).

Pyrenophorin (VI): $^1$H NMR ($CD_3CN$, 600 MHz) δ 6.91 (2H, d, $J_{H-3,H-2}$=15.94, H-3), 6.42 (2H, d, $H_{H-2,H-3}$=15.94, H-2), 4.97 (2H, m, H-7), 2.62 (4H, m, H-5), 2.04 (4H, m, H-6), 1.24 (6H, d, $J_{CH3,H-7}$=6.27, CH3); $^{13}$C NMR ($CD_3CN$, 150 MHz, from HSQC and HMBC correlations) δ 201.6 (2×C, C-4), 166.4 (2×C, C-1), 140.7 (2×CH, C-3), 131.9 (2×CH, C-2), 73.3 (2×CH, C-7), 37.5 (2×$CH_2$, C-5), 32.5 (2×$CH_2$, C-6), 19.8 (2×$CH_3$, $CH_3$); HRMS m/z 309.1331 $[M+H]^+$ (calc. for $[C_{16}H_{21}O_6]^+$, 309.1333).

The results of the endophyte isolation and screening including the five strains used in this study showed that the species appear to be of *Lophodermium*. Compounds 1, (IIa), (IIb), and (III)-(VI) represent the major metabolites isolated from these strains with compounds 1, (III) and (IV) showing antifungal activity to both a representative ascomycete, *S. cerevisae* and a rust (*M. violaceum*) that is biologically similar to white pine blister rust. This present work demonstrates that deliberately selected superior white pine trees from New Brunswick, Nova Scotia, Quebec and Prince Edward Island Canada harbour needle endophytes that produced extracts that were toxic to a representative ascomycete. After these experiments were initiated, Ganley et al., (2008) reported that mixed inoculations of undefined endophytes in western white pine seedlings resulted in tolerance independent of plant genotype. These authors ruled out the production of antifungal extracts as the mechanistic basis (competitive habitat exclusion). They suggested that the tolerance was due to a form of induced resistance. The present work would appear to support competitive exclusion as an important mechanism. Although metabolites of red and white spruce did possess antifungal activity to S. cerevisae (Sumarah et al., 2008b, 2010), their potency was much less than the compounds isolated from the pine endophytes studied.

Discussion

The screening of fungal extracts isolated from P. strobus resulted in the discovery of three new compounds (1, (IIa) and (IIb)) a new natural product (III) and three previously described antifungal metabolites ((IV-(VI)) as the major constituents. The five strains studied are currently being evaluated for their ability to provide tolerance of P. strobus trees against C. ribicola in eastern North America.

4. Experimental 4.1. General Experimental Procedures

LC-HRMS data were acquired on a system consisting of an Agilent 1200 series HPLC, equipped with an Agilent 1100 series binary pump, connected to an Agilent G1969A LC/MSD TOF HRMS. Extracts or isolated compounds were separated on a ZORBAX Eclipse Plus (C-18; 1.8 µm) 3.0×50 mm HPLC column with a 1 mL/min gradient of $CH_3CN/H_2O$+0.1% formic acid (10:90 to 95:5 over 5 min). Chiral LC-HRMS analysis was performed using a Kromasil 3-AmyCoat RP 4.6×150 mm column and an isocratic mobile phase $CH_3CN/H_2O$ (40:60)+0.1% formic acid with a 1 mL/min flow rate. The MS instrument was operated in both positive and negative ion mode with the following settings: drying gas temperature 350° C., nebulizer pressure 60 psi, drying gas 13 L/min and spray voltage 4000 V. The LC-MS-SPE system consisted of an Agilent 1100 series HPLC, Knauer WellChrom K-120 solvent pump (post-column dilution), Accurate ICP-04-20 flow-splitter by LC Packings, Bruker Esquire 4000 ion trap mass spectrometer, Agilent G1315B Photodiode Array Detector, Bruker/Spark Prospekt II LC-SPE-NMR interface module with $N_2$-blanketing of the SPE compartment and an additional GP resin cartridge placed in a clamp holder in the waste outlet leading to an Agilent G1315A variable wavelength absorbance detector for monitoring, all managed by Bruker HyStar/EsquireControl software v. 3.0. (See Kesting et al., 2010 for system schematic). The samples were filtered through 0.45 µm GHP Acrodisc (13 mm) syringe filters prior to injections, and separation was achieved on a Phenomenex Synergi Max-RP (C-12; 4 µm) 250 mm×4.6 mm column, using a $CH_3CN$—$H_2O$ gradient (20:80-100:0 over 25 min). A flow rate of 0.75 mL/min was used, as well as a postcolumn makeup flow of $H_2O$ (1.25 mL/min) was added to reduce the solvent strength for trapping on Spark Hysphere Resin GP 10×2 mm SPE cartridges. Cartridges were dried for 45 minutes prior to elution, using pressurized $N_2$-gas. Trapped peaks were eluted into 3 mm (335-PP) NMR tubes from Wilmad, using 160 µL of $CD_3CN$, and NMR data were acquired using a Varian 600 MHz spectrometer equipped with a 5 mm HCN PFG Chili-Probe (cryogenic) operating at 599.92 MHz for $^1H$ NMR. Chemical shifts were referenced to the residual solvent peak (1.94 ppm for $CD_3CN$). Optical rotation was measured on a Perkin-Elmer 341 polarimeter.

4.2. Fungal Strains

The five fungal strains were all isolated from P. strobus trees originating in Nova Scotia, New Brunswick and Prince Edward Island, Canada and deposited in the CBS culture collection in The Netherlands. These strains were selected via a screening process from a collection of P. strobus needle endophytes isolated in 2005 from trees maintained in the J.D. Irving Ltd plantation, located in Sussex, NB.

4.3. Toxicity Testing

Disc diffusion assays with the extracts were employed for preliminary antifungal testing using Saccharomyces cerevisae for all strains (Sumarah et al., 2008b). The characterized compounds 1, (III) and (IV) were also tested for antifungal activity against both the rust M. violaceum grown on MYP (malt, yeast, peptone media) Zhang et al., 2008 and S. cerevisae (1 g/L glucose and noble agar). The individual compounds were further tested using these two fungi in 96 well microplates where 10 µL of 1 mg/mL (~4 µM) of each compound in DMSO was added to 200 µL of the above macerated cultures. The plates were incubated at room temperature with constant shaking and were measured at 600 nm. The antifungal compound nystatin was used as the positive control for all experiments.

4.4. DNA Sequencing

DNA was extracted from the endophyte cultures using an UltraClean DNA isolation kit (MO BIO Laboratories 12224-250) as previously described (Sumarah et al. 2008b). The PCR primers used were ITS4 (5' TCC TCC GCT TAT TGA TAT GC 3') (SEQ ID NO:1) and ITS1F (5' CTT GGT CAT TTA GAG GAA GTA A 3') (SEQ ID NO:2). Sequencing was performed by DNA L and Marks, Saint-Jean-sur-Richelieu, Quebec.

4.5. Fermentation, Extraction and Isolation

All strains were stored on 2% MEA (malt extract agar, Difco) slants at 5° C. and fermented on a 5 L scale in Glaxo bottles containing 1 L of 2% ME medium for 2 months (20° C.). The cultures were then harvested, filtered, extracted with 2×equal volumes of EtOAc and dried by rotary evaporation. The extracts were screened by LC-HRMS using electrospray ionization in both positive and negative ion mode. The major metabolites from the five extracts were separated and isolated using the LC-MS-SPE setup described in 4.1. Isolation of compounds was based on absorbance threshold levels at 220 nm for CBS 127939, CBS 127941 and CBS 127940, and at 225 nm for CBS 127942 and CBS 127939. From CBS 127939 three compounds were isolated as major metabolites. CBS 127942 and CBS 127939 are almost identical based on the UV chromatogram with four identical compounds and one additional from CBS 127942. CBS 127940 and CBS 127941 also had similar chromatograms each containing three identical metabolites with two additionally compounds isolated from CBS 127941.

4.6. Compound 1

(2Z,4E)-methyl 6-acetoxy-5-formyl-7-oxo-octa-2,4-dienoate: $[\alpha]^{25}_D$=−4.3 (c 0.1, $CHCl_3$); $^1H$ NMR and $^{13}C$ NMR data see Table 2; HRMS m/z 277.0682 [M+Na]$^+$ (calc. for $[C_{12}H_{14}O_6Na]^+$, 277.0683).

4.8. Compound (IIa)

(E)-5-(hydroxymethyl)-2-(6'-methylhept-2'-en-2'-yl)phenol: $^1H$ NMR and $^{13}C$ NMR data see Table 3; HRMS m/z 257.1583 [M+Na]$^+$ (calc. for $[C_{15}H_{22}O_2Na]^+$, 257.1512).

4.9. Compound (IIb)

(Z)-5-(hydroxymethyl)-2-(6'-methylhept-2'-en-2'-yl)phenol: $^1$H NMR and $^{13}$C NMR data see Table 3; HRMS m/z 257.1513 [M+Na]$^+$ (calc. for [C$_{15}$H$_{22}$O$_2$Na]$^+$, 257.1512).

4.7. Compound (III)

5-(hydroxymethyl)-2-(2',6',6'-trimethyltetrahydro-2H-pyran-2-yl)phenol: $[\alpha]^{25}_D$=0 (c 0.1, CHCl$_3$); $^1$H NMR and $^{13}$C NMR data see Table 3; HRMS m/z 273.1460 [M+Na]$^+$ (calc. for [C$_{15}$H$_{22}$O$_3$Na]$^+$, 273.1461).

4.10. Compound (IV)

Pyrenophorol (IV): $^1$H NMR (CD$_3$CN, 600 MHz) δ 6.78 (2H, dd, J$_{H-3,H-2}$=15.76, J$_{H-3,H-4}$=6.66, H-3), 5.82 (2H, dd, J$_{H-2,H-3}$=15.76, J$_{H-2,H-4}$=1.16, H-2), 4.99 (2H, m, H-7), 4.06 (2H, m, H-4), 3.21 (2H, d, J$_{OH,H4}$=4.37, OH) 1.76 (2H, m, H-5A), 1.68 (2H, m, H-6A), 1.64 (2H, m, H-5B), 1.51 (2H, m, H-6B), 1.21 (6H, d, J$_{CH3,H-7}$=6.56, CH$_3$); $^{13}$C NMR (CD$_3$CN, 150 MHz, from HSQC and HMBC correlations) δ 166.7 (2×C, C-1), 150.4 (2×CH, C-3), 122.4 (2×CH, C-2), 71.0 (2×CH, C-4), 70.5 (2×CH, C-7), 31.4 (2×CH$_2$, –5), 29.4 (2×CH$_2$, C-6), 18.5 (2×CH$_3$, CH$_3$); HRMS m/z 313.1648 [M+H]$^+$ (calc. for [C$_{16}$H$_{25}$O$_6$]$^+$, 313.1646).

4.11. Compound (V)

Dihydropyrenophorin (V): $^1$H NMR (CD$_3$CN, 600 MHz) δ 6.93 (1H, dd, J$_{H3,H2'}$=15.72, J$_{H3,H4}$=4.49, H-3'), 6.87 (1H, d, J$_{H-3,H-2}$=16.15, H-3), 6.52 (1H, d, J$_{H2,H3}$=16.15, H-2), 5.89 (1H, d, J$_{H2,H3}$=15.72, J$_{H-1',H-4'}$=1.66, H-2'), 5.05 (1H, m, H-7'), 4.91 (1H, m, H-7), 2.71 (1H, ddd, J$_{H-5A,H-5B}$=13.7, J$_{H-5A,H6}$=9.3, J$_{H5A,H6}$=4.11, H-5A), 2.60 (1H, m, H-5B), 2.01 (2H, m, H-6), 1.85 (1H, m, H-6A), 1.76 (1H, m, H-6B, 1.73 (1H, m, H-5'A), 1.60 (1H, m, H-5'B), 1.23 (3H, d, J$_{H-7'-CH3, H-7'}$=6.51, 7'-CH$_3$), 1.20 (3H, d, J$_{7-CH3, H-7}$=6.27, 7-CH$_3$); $^{13}$C NMR (CD$_3$CN, 150 MHz, from HSQC and HMBC correlations) δ 203.0 (C, C-4), 167.3 (C, C-1'), 166.1 (C, C-1), 150.4 (CH, C-3'), 140.7 (CH, C-3), 131.9 (CH, C-2), 71.9 (CH, C-7'), 71.0 (CH, C-7), 69.7 (CH, C-4'), 36.2 (CH$_2$, C-5), 32.6 (CH$_2$, C-6), 31.4 (CH$_2$, C-5'), 28.5 (CH$_2$, C-6'), 19.8 (CH$_3$, 7-CH$_3$), 18.1 (CH$_3$, 7'-CH$_3$); HRMS m/z 311.1481 [M+H]$^+$ (calc. for [C$_{16}$H$_{23}$O$_6$]$_+$, 311.1489).

4.12. Compound (VI)

Pyrenophorin (VI): $^1$H NMR (CD$_3$CN, 600 MHz) δ 6.91 (2H, d, =15.94, H-3), 6.42 (2H, d, J$_{H-2,H-3}$=15.94, H-2), 4.97 (2H, m, H-7), 2.62 (4H, m, H-5), 2.04 (4H, m, H-6), 1.24 (6H, d, J$_{CH3,H-7}$=6.27, CH$_3$); $^{13}$C NMR (CD$_3$CN, 150 MHz, from HSQC and HMBC correlations) δ 201.6 (2×C, C-4), 166.4 (2×C, C-1), 140.7 (2×CH, C-3), 131.9 (2×CH, C-2), 73.3 (2×CH, C-7), 37.5 (2×CH$_2$, C-5), 32.5 (2×CH$_2$, C-6), 19.8 (2×CH$_3$, CH$_3$); HRMS m/z 309.1331 [M+H]$^+$ (calc. for [C$_{16}$H$_{21}$O$_6$]$^+$,309.1333).

TABLE 1

Metabolite production from strains studied.

| Strain | 1 | (III) | (IIa) | (IIb) | (IV) | (V) | (VI) |
|---|---|---|---|---|---|---|---|
| CBS 127939 | | | | | + | + | + |
| CBS 127938 | + | + | + | | + | | |
| CBS 127940 | | + | + | + | | | |
| CBS 127942 | + | + | + | + | + | | |
| CBS 127941 | | + | + | + | + | | + |

+ indicating the presence of the metabolite in the extract

TABLE 2

$^1$H (600 MHz) and $^{13}$C (150 MHz) NMR spectral data for compound 1 in CD$_3$CN.

| Position | δ$_C$ | δ$_H$, (J in Hz) | HMBC$_{H→C}$ |
|---|---|---|---|
| 1 | 166.9 | | |
| 2 | 128.5 | 6.22 (dd, J$_{2,3}$ = 11.4, | 4 |
| 3 | 136.6 | J$_{2,4}$ = 0.8) | 1, 5 |
| 4 | 146.8 | 7.23 (dd, J$_{3,2}$ = 11.4, | 2, 6, 7 |
| 5 | 140.6 | J$_{3,4}$ = 11.8) | |
| 6 | 72.4 | 8.39 (dd, J$_{4,3}$ = 11.8, | 4, 5, 7, 8, 10 |
| 7 | 194.4 | J$_{4,2}$ = 0.8) | 5, 6 |
| 8 | 202.9 | | |
| 9 | 26.7 | 6.15 (s) | 6, 8 |
| 10 | 170.4 | 9.57 (s) | |
| 11 | 21.1 | | 10 |
| 12 | 52.5 | 2.11 (s) | 1 |
| | | 2.08 (s) | |
| | | 3.76 (s) | |

TABLE 3

$^1$H (600 MHz) and $^{13}$C (150 MHz) NMR data for compounds (IIa), (IIb) and (III) in CD$_3$CN.

| Position | III | | | IIa | | | IIb | | |
|---|---|---|---|---|---|---|---|---|---|
| | δ$_C$ | δ$_H$,(J in Hz) | HMBC$_{H→C}$ | δ$_C$ | δ$_H$,(J in Hz) | HMBC$_{H→C}$ | NOE | δ$_C$ | δ$_H$,(J in Hz) | NOE |
| 1 | 157.5 | | | 153.7 | | | | | | |
| 2 | 130.8 | | | 130.7 | | | | | | |
| 3 | 126.1 | 7.07 (d, J$_{3,4}$ = 7.9) | 1, 5, 2' | 130.0 | 7.00 (d, J$_{3,4}$ = 7.9) | 1, 5, 2' | 9' | 129.7 | 6.95 (d, J$_{3,4}$ = 8.0) | |
| 4 | 118.8 | 6.78 (dd, J$_{4,3}$= 7.9, J$_{4,6}$ = 1.6) | 2, 6, 7 | 118.8 | 6.76 (d, J$_{4,3}$ = 7.9) | 2, 6, 7 | | 118.3 | 6.81 (d, J$_{4,3}$ = 8.0) | |
| 5 | 142.8 | | | 142.4 | | | | 144.4 | | |
| 6 | 116.5 | 6.73 (d, J$_{6,4}$ = 1.6) | 2, 4, 7 | 114.4 | 6.76 (s) | 2, 4, 7 | | 113.7 | 6.81(s) | |
| 7 | 64.5 | 4.48 (d, J$_{7,7—OH}$ = 5.9) | 4, 5, 6 | 63.9 | 4.46 (d, J$_{7,7—OH}$ = 5.9) | 4, 5, 6 | | 63.7 | 4.50 (d, J$_{7,7—OH}$ = 6.0) | |
| 2' | 78.5 | | | 131.5 | | | | 128.6 | | |
| 3' | 34.8 | A: 2.43 (ddd, J$_{3'A,3'B}$ = 14.1, J$_{3'A,4'A}$ = 4.79, J$_{3'A,4'B}$ = 3.3) B: 1.62 (ddd, J$_{3'B,3'A}$= 14.1, J$_{3'B,4'B}$ = 11.9, J$_{3'B,4'A}$ = 3.7) | | 130.8 | 5.43 (tq, J$_{3',4'}$ = 7.2, J$_{3',9'}$ = 0.7) | 3', 4', 9' | | 130.2 | 5.55 (tq, J$_{3',4'}$ = 7.2, J$_{3',9}$ = 1.8) | 9' |

TABLE 3-continued $^1$H (600 MHz) and $^{13}$C (150 MHz) NMR data for compounds (IIa), (IIb) and (III) in CD$_3$CN.

| Position | III | | | IIa | | | | IIb | | |
|---|---|---|---|---|---|---|---|---|---|---|
| | $\delta_C$ | $\delta_H$(J in Hz) | HMBC$_{H \to C}$ | $\delta_C$ | $\delta_H$(J in Hz) | HMBC$_{H \to C}$ | NOE | $\delta_C$ | $\delta_H$(J in Hz) | NOE |
| 4' | 17.6 | A: 1.73 (ddd, J$_{4'A,4'B}$ = 14.6, J$_{4'A,5'}$ = 7.6, J$_{4'A,3'B}$ = 3.7) B: 1.68 (m) | | 25.9 | 2.14 (m) | 2', 3', 5' | | 27.2 | 1.79 (m) | |
| 5' | 37.8 | 1.52 (dd, J$_{5',4'A}$ = 7.6, J$_{5',4'B}$ = 4.6) | 2', 3', 4', 7',8' | 38.6 | 1.32 (q, J$_{5',4'}$ = J$_{5',6'}$ = 7.0) | 3', 4', 6', 7' + 8' | | 38.8 | 1.20 (q, J$_{5',4'}$ = J$_{5',6'}$ = 7.6) | |
| 6' | 75.3 | | | 28.5 | 1.61 (m) | | | 28.3 | 1.45 (m) | |
| 7' | 32.6 | 1.23 (s) | 5', 6', 8' | 23.0 | 0.92 (d, J$_{7',6'}$ = J$_{8',6'}$ 6.6) | 5', 6', 7' + 8' | 3 | 22.5 | 0.78 (d, J$_{7',6'}$ = J$_{8',6'}$ 6.6) | |
| 8' | 25.7 | 0.93 (s) | 5', 6', 9' | 23.0 | 0.92 (d, J$_{7',6'}$ = J$_{8',6'}$ 6.6) | | | 22.5 | 0.78 (d, J$_{7',6'}$ = J$_{8',6'}$ 6.6) | |
| 9' | 32.0 | 1.43 (s) | 2, 2', 3' | 17.6 | 1.93 (d, J$_{9',3'}$ = 0.7$^d$) | 2, 2' | | 24.4 | 1.93 | 3' |
| 1-OH | | 9.06 (s) | | | 6.61 (s) | 2, 5, 6 | | | 6.33 (s) | |
| 7-OH | | 3.10 (t, J$_{7',-OH,7}$ = 5.9) | | | 3.11 (t, J$_{7-OH,7}$ = 5.9) | | | | 3.09 (t, J$_{7-OH,7}$ = 6.0) | |

TABLE 4

```
SEQ ID    1071-2      CATTAAAGAATACATGGCCTTCGGGTCCTATTCTCACCCTT
NO: 3     CBS127939   TGTTTACCAAAACTCTTGTTGCCTTGGCGCATTCGTGCGCC
                      AAAGGAATCAAACCCTTGAATCTCTGCTGTCTGAGTACTAT
                      ATAATAGTTA

SEQ ID    860-2       CATTAAAGAATACATGGCCTTCGGGCCCTATTCTCACCCTT
NO: 4     CBS 127938  TGTTTACCAAAACTCTTGTTGCCTTGGCGCATTCGTGCGCC
                      AAAGGAATCAAACCCTTGAATCTCTGCTGTCTGAGTACTAT
                      ATAATAGTTAAAACTTTCAACAACGGATCTCTTGGTTCTGG
                      CATCGATGAAGAACGCAGCGAAATGCAATAAGTAATGTGA
                      ATT

SEQ ID    3625-2      CATTAAAGAATACATGGCCTTCGGGTCCTATTCTCACCCTT
NO: 5     CBS127942   TGTTTACCAAAACTCTTGTTGCCTTGGCGCATTCGTGCGCC
                      AAAGGAATCAAACCCTTGAATCTCTGCTGTCTGAGTACTAT
                      ATAATAGTTAAAACTTTCAACAACGGATCTCTTGGTTCTGG
                      CATCGATGAAGAACGCAGCGAAATGCGATAAGTAATGTGA
                      ATTGCAGAATTCATGAATCATCGAATCTTTGAACGCACATT
                      GCGCCTCCTGGTATTCCGGGAGGCATGCCTGTTCGAGCGT
                      CCTTACAACCCTCAA

SEQ ID    1517-2      CATTACAACCCTCAAGCTCTGCTTGGTATTGGGCTCGCCTC
NO: 6     CBS127940   CTTTGGCCTGCCTCAAAATCAGTGGCGGCACAGTCCGATC
                      CTCAAGCGCAGTAATACACGACGCTTGCCGGTGAAGGTTG
                      CTGCTCCAGAAACCCCCACAAACTAAAGGTTGACCTCGG
                      ATCAGGTAGGGATACCCGCTGAACTTAAGCATATCAATA

SEQ ID    1747-1      CATTACAACCCTCAAGCTCTGCTTGGTATTGGGCTCGCCTC
NO: 7     CBS127941   CTTTGGCCTGCCTCAAAATCAGTGGCGGCACAGTCCGATC
                      CTCAAGCGCAGTAATACACGACGCTTGCCGGTGAAGGTTG
                      CTGCTCCCGAAACCCCCACAAACTAAAGGTTGACCACGG
                      ATCATGTAGGGATACCCGCTGAACTTAAGCATA
```

Example 2

Testing of Endophyte Strains for Ability to Provide Protection to *P. Strobus* trees against *C. ribiola*

The five strains studied are currently being evaluated for their ability to provide protection to *P. strobus* trees against *C. ribicola* in eastern North America.

Example 3

Disc diffusion tests using *C. Ribicola* as the test pathogen will be conducted.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications, are herein incorporated by reference in their entirety to the same extent as if each individual publication, patent or patent application was specifically and individually indicated to be incorporated by reference in its entirety.

CITATIONS FOR REFERENCES REFERRED TO IN THE SPECIFICATION

Deckert, R. J., Hsiang, T., Peterson, L. R., 2002. Genetic relationships of endophytic *Lophodermium nitens* isolates from needles of *Pinus strobes*. Mycol. Res. 106, 305-313.

Ganley, R. J., Sniezko, R. A., Newcombe, G., 2008. Endophyte-mediated resistance against white pine blister rust in *Pinus monticola*. Forest Ecol. Manag. 255, 2751-2760.

Johnson J A and Whitney N J. 1992. Isolation of fungal endophytes from black spruce (*Picea meriana*) dormant buds and needles from New Brunswick, Canada. Canadian Journal of Botany 70: 1754-57.

Kesting, J. R., Huang, J., Sørensen, D., 2010. Identification of adulterants in Gold Nine Soft Capsules by LC-HRMS and LC-MS-SPE/NMR and comparative in-vivo study with standards in a hypertensive rat model. J. Pharm. Biomed. Anal. 51, 705-711.

Krohn, K., Farooq, U., Flörke, U., Schulz, B., Draeger, S., Pescitelli, G., Salvadori, P., Sándor, A., Kurtán, T., 2007. Secondary metabolites isolated from an endophytic *Phoma* sp.—Absolute configuration of tetrahydropyrenophorol using the solid-state TDDFT CD methodology. Eur. J. Organic Chem. 19, 3206-3211.

Miller, J. D., Mackenzie, S., Foto, M., Adams, G. W., Findlay, J. A., 2002. Needles of white spruce inoculated with rugulosin-producing endophytes contain rugulosin reducing spruce budworm growth rate. Mycol. Res. 106, 471-479.

Miller, J. D., Sumarah, M. W., Adams, G. W., 2008. Effect of a rugulosin-producing endophyte in *Picea glauca* on *Choristoneura fumiferana*. J. Chem. Ecol. 34, 362-368.

Serra, S., 2000. Bisabolane sesquiterpenes: Synthesis of (R)-(+)-sydowic acid and (R)-(+)-curcumene ether. Synlett. 6, 890-892.

Sumarah, M. W., Adams, G. W., Berghout, J., Slack, G. J., Wilson, A. M., Miller, J. D., 2008a. Spread and persistence of a rugulosin-producing endophyte in white spruce seedlings. Mycol. Res. 112, 731-736.

Sumarah, M. W., Puniani, E., Blackwell, B. A., Miller, J. D., 2008b. Characterization of polyketide metabolites from foliar endophytes of *Picea glauca*. J. Nat. Prod. 71, 1393-1398.

Sumarah, M. W. and Miller, J. D., 2009. Anti-insect secondary metabolites from fungal endophytes of conifer trees. Nat. Prod. Commun. 4, 1497-1504.

Sumarah, M. W., Puniani, E., Sørensen, D., Blackwell, B. A., Miller, J. D., 2010. Secondary metabolites from anti-insect extracts of endophytic fungi isolated from *Picea rubens*. Phytochemistry 71, 760-765.

Vincent, J. G. Vincent, H. W., 1944, Filter paper disc modification of the Oxford cup penicillin determination. Prof. Soc. Exp. Biology Med. 55, 162-164.

Zhang, K., Egold, H., Draeger, S., Schulz, B., 2008. Diversity of antimicrobial pyrenophorol derivatives from an endophytic fungus, *Phoma* sp. Eur. J. Organic Chem. 25, 4320-4328.

The invention claimed is:

1. A method of colonizing a nursery grown white pine seedling with a toxigenic endophyte comprising: 1) selecting a toxigenic endophyte producing a compound selected from a compound of the formula (I), (II), (III), (IV), (V) and/or (VI); 2) mechanically inoculating the nursery grown white pine seedling or a white pine seed with an inoculum composition comprising hyphal fragments of the toxigenic endophyte at a concentration of at least 0.2 hyphal fragments per microliter, during a susceptible time window when the white pine seedling or white pine seed is susceptible to colonization by the toxigenic endophyte, 3) growing the inoculated seedling or seed under conditions, wherein the toxigenic endophyte colonizes the seedling and produces a toxigenic amount of a compound selected from a compound of the formula (I), (II), (III), (IV), (V) and/or (VI), wherein the compound is selected from a compound of the formula (I)

(I)

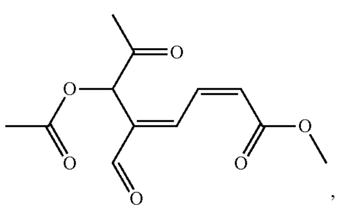

, in all their stereoisomeric forms and mixtures thereof in any ratio, and their physiologically tolerable salts;

a compound of the formula (II)

(II)

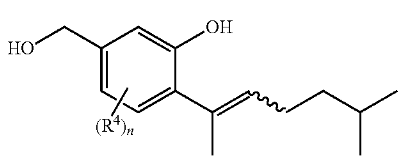

wherein $R^4$ is independently or simultaneously H, halo, OH, or $CH_3$, n is an integer between 0 and 3, in all their stereoisomeric forms and mixtures thereof in any ratio, and their physiologically tolerable salts;

a compound of the formula (III)

(III)

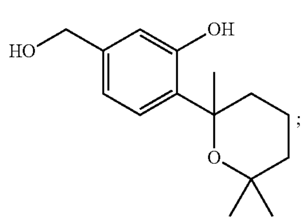

;

a compound the formula (IV)

(IV)

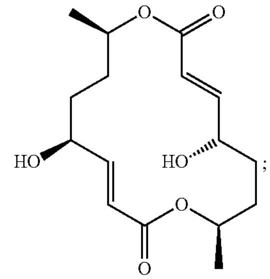

;

a compound of the formula (V)

(V)

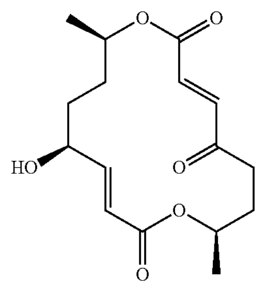

and/or;

a compound of formula (VI)

(VI)

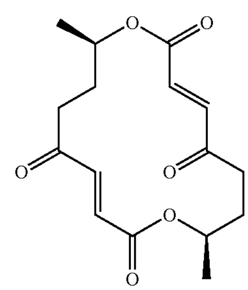

.

2. The method of claim 1, wherein the susceptible time window for the white pine seedling comprises the period post germination during sustained elongation of the seedling shoot apex when the number of intermediately developed and juvenile needles is greater than the number of needles that are completely developed and mature and the susceptible time window for the white pine seedling is during seed stratification.

3. The method of claim 1, comprising colonizing a population of seedlings or preparing a population of seedlings with increased tolerance to a pest comprising inoculating one or more white pine conifer seedlings and/or one or more white pine seeds, wherein the composition comprises one or more selected toxigenic endophytes, under conditions wherein at least one toxigenic endophyte colonizes the seedling and produces a compound of the formula (I), (II), (III), (IV), (V) and/or (VI).

4. The method of claim 1, wherein the compound is selected from a compound of the formula (IV), (V), or (VI) selected from pyrenophorol, dihydropyrenophorin and pyrenophorin.

5. The method of claim 1 wherein one of the one or more endophytes comprises an endophyte of the *Lophodermium* species.

6. The method of claim 1, wherein at least one of the one or more toxigenic endophytes produces one or more compounds selected from a compound of the formula (I), (II) and/or (III).

7. The method of claim 1, wherein the one or more endophytes comprises:
   a) a strain having all of the identifying characteristics of a strain deposited under the Accession number CBS 127938, CBS 127940, CBS 127941, and/or CBS 127942, deposited Sep. 29, 2010, Centraalbureau voor Schimmelcutures, Uppsalalaan 8, P.O. Box 851673508 AD Utrecht, The Netherlands;
   b) an endophyte comprising any one of SEQ ID NO: 4 to 7; and/or
   c) an endophyte comprising an Internal Transcribed Spacer (ITS) region having at least 99% sequence identity to any one of the sequences in b).

8. The method of claim 1, wherein the inoculating comprises mechanically spraying the seedling or seedlings with the composition comprising the toxigenic endophyte.

9. The method of claim 1, wherein the inoculating step comprises contacting the white pine seed with the composition during seed stratification.

10. The method of claim 9, wherein the white pine seed is contacted with the composition by soaking the seed in the composition.

11. The method of claim 1, wherein the toxin compound or in the white pine seedling is in sufficient amount to reduce pest infection rate or growth compared to a control non-inoculated white pine seedling.

12. The method of claim 11, wherein the toxin compound is present in a white pine needle in an amount of at least 0.15 microgram per gram of needle.

13. The method of claim 1, wherein the white pine seedling has a shoot length that is greater than 10 mm and less than 100 mm.

14. The method of claim 1, wherein the pest is a fungus associated with disease.

15. The method of claim 1, wherein the selected toxigenic endophyte is isolated from a donating plant and cultured, wherein the toxigenic endophyte produces a compound selected from a compound of formula I, II III, and/or IV.

16. The method of claim 1 wherein the compound of the formula (II) is a compound of the formula (IIa) and/or (IIb)

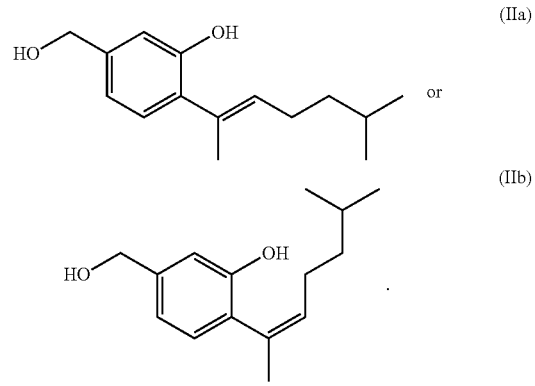

17. The method of claim 1, wherein one of the one or more endophytes comprises an endophyte of the *Lophodermium* strain having all of the identifying characteristics as a strain deposited under the accession number CBS 127939, deposited Sep. 29, 2010, Centraalbureau voor Schimmelcutures, Uppsalalaan 8, P.O. Box 851673508 AD Utrecht, The Netherlands; an endophyte comprising SEQ ID NO:3, and/or an endophyte comprising an Internal Transcribed Spacer (ITS) region having at least 99% sequence identity to SEQ ID NO:3.

18. The method of claim 10, wherein the pine seed is soaked is overnight.

19. The method of claim 18, wherein the pine seed is further refrigerated at 2-6° C.

20. The method of claim 11, wherein the pest infection rate or growth is inhibited by at least 5% relative to the control or by at least 10% relative to the control.

21. The method of claim 1, wherein the conditions comprise an environment of controlled high humidity of at least 70%.

22. The method of claim 14, wherein the fungus associated with disease is a rust fungus.

23. The method of claim 22, wherein the rust fungus is *Cronartium ribicola*, and/or *Microbotryum violaceum*.

24. The method of claim 15, wherein the cultured toxigenic endophyte is harvested and resuspended in a diluent.

* * * * *